US012799522B2

(12) United States Patent
Chew et al.

(10) Patent No.: US 12,799,522 B2
(45) **Date of Patent: *Nov. 17, 2026**

(54) METHODS, COMPOSITIONS, AND KITS FOR BLOCKING A CAPTURE PROBE ON A SPATIAL ARRAY

(71) Applicant: 10x Genomics, Inc., Pleasanton, CA (US)

(72) Inventors: Jennifer Chew, Hayward, CA (US); David Michael Patterson, Oakland, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 458 days.

This patent is subject to a terminal disclaimer.

(21) Appl. No.: 18/492,362

(22) Filed: Oct. 23, 2023

(65) Prior Publication Data

US 2024/0043908 A1 Feb. 8, 2024

Related U.S. Application Data

(63) Continuation of application No. 18/226,933, filed on Jul. 27, 2023, now Pat. No. 11,840,724, which is a continuation of application No. 18/181,263, filed on Mar. 9, 2023, now Pat. No. 11,753,673, which is a continuation of application No. PCT/US2022/042320, filed on Sep. 1, 2022.

(60) Provisional application No. 63/239,612, filed on Sep. 1, 2021.

(51) Int. Cl.
*C12Q 1/68* (2018.01)
*C12Q 1/6806* (2018.01)

(52) U.S. Cl.
CPC .................................. *C12Q 1/6806* (2013.01)

(58) Field of Classification Search
CPC .................................................... C12Q 1/6837
See application file for complete search history.

(56) References Cited

U.S. PATENT DOCUMENTS 4,683,195 A 7/1987 Mullis
4,683,202 A 7/1987 Mullis
4,800,159 A 1/1989 Mullis
4,883,867 A 11/1989 Lee
4,965,188 A 10/1990 Mullis
4,988,617 A 1/1991 Landegren et al.
5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,494,810 A 2/1996 Barany et al.
5,503,980 A 4/1996 Cantor
5,512,439 A 4/1996 Hornes
5,512,462 A 4/1996 Cheng
5,582,977 A 12/1996 Yue
5,599,675 A 2/1997 Brenner
5,641,658 A 6/1997 Adams
5,648,245 A 7/1997 Fire et al.
5,658,751 A 8/1997 Yue
5,695,940 A 12/1997 Drmanac et al.
5,750,341 A 5/1998 Macevicz
5,763,175 A 6/1998 Brenner
5,830,711 A 11/1998 Barany et al.
5,837,832 A 11/1998 Chee et al.
5,854,033 A 12/1998 Lizardi
5,863,753 A 1/1999 Haugland
5,871,921 A 2/1999 Landegren et al.
5,912,148 A 6/1999 Eggerding
5,925,545 A 7/1999 Reznikoff et al.
5,928,906 A 7/1999 Koester et al.
5,958,775 A 9/1999 Wickstrrom
5,962,271 A 10/1999 Chenchik et al.
5,962,272 A 10/1999 Chenchik et al.
(Continued)

FOREIGN PATENT DOCUMENTS

AU 2003200718 10/2006
CN 1273609 11/2000
(Continued)

OTHER PUBLICATIONS

Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Extended European Search Report in European Appln. No. 24215617.2, dated Apr. 14, 2025, 7 pages.
Kishi et al., "Light-Seq: light-directed in situ barcoding of biomolecules in fixed cells and tissues for spatially indexed sequencing," Nature Methods, Oct. 10, 2022, 19(11):1393-1402.
(Continued)

*Primary Examiner* — Kenneth R Horlick
(74) *Attorney, Agent, or Firm* — Fish & Richardson P.C.

(57) ABSTRACT

Provided herein are methods, compositions, and kits for reducing and/or eliminating binding of analytes to capture probes of an array. The methods, compositions, and kits can include terminal deoxynucleotidyl transferase and dideoxynucleotides. In an exemplary embodiment, disclosed methods include (a) disposing a biological sample onto an array at a first area, wherein the array comprises a plurality of capture probes comprising a spatial barcode and a capture domain, wherein a first capture probe is comprised in the first area of the array; and a second area of the array comprises a second capture probe, wherein the second area is not covered by the biological sample disposed on the array; and (b) contacting the second area of the array with a solution comprising terminal deoxynucleotidyl transferase and one or more dideoxynucleotides, such that a dideoxynucleotide is incorporated into the second capture probe.

20 Claims, 3 Drawing Sheets

(56) References Cited

U.S. PATENT DOCUMENTS

| | | | |
|---|---|---|---|
| 5,965,443 | A | 10/1999 | Reznikoff et al. |
| 6,013,440 | A | 1/2000 | Lipshutz |
| 6,027,889 | A | 2/2000 | Barany et al. |
| 6,054,274 | A | 4/2000 | Sampson et al. |
| 6,060,240 | A | 5/2000 | Kamb et al. |
| 6,130,073 | A | 10/2000 | Eggerding |
| 6,143,496 | A | 11/2000 | Brown |
| 6,153,389 | A | 11/2000 | Haarer |
| 6,159,736 | A | 12/2000 | Reznikoff et al. |
| 6,165,714 | A | 12/2000 | Lane et al. |
| 6,210,891 | B1 | 4/2001 | Nyren |
| 6,210,894 | B1 | 4/2001 | Brennan |
| 6,214,587 | B1 | 4/2001 | Dattagupta |
| 6,251,639 | B1 | 6/2001 | Kurn |
| 6,258,568 | B1 | 7/2001 | Nyren |
| 6,266,459 | B1 | 7/2001 | Walt |
| 6,268,148 | B1 | 7/2001 | Barany et al. |
| 6,274,320 | B1 | 8/2001 | Rothberg |
| 6,291,180 | B1 | 9/2001 | Chu |
| 6,291,187 | B1 | 9/2001 | Kingsmore et al. |
| 6,300,063 | B1 | 10/2001 | Lipshutz et al. |
| 6,309,824 | B1 | 10/2001 | Drmanac |
| 6,323,009 | B1 | 11/2001 | Lasken et al. |
| 6,344,316 | B1 | 2/2002 | Lockhart |
| 6,344,329 | B1 | 2/2002 | Lizardi et al. |
| 6,355,431 | B1 | 3/2002 | Chee |
| 6,368,801 | B1 | 4/2002 | Faruqi |
| 6,401,267 | B1 | 6/2002 | Drmanac |
| 6,404,907 | B1 | 6/2002 | Gilchrist |
| 6,432,360 | B1 | 8/2002 | Church et al. |
| 6,503,713 | B1 | 1/2003 | Rana |
| 6,506,561 | B1 | 1/2003 | Cheval et al. |
| 6,534,266 | B1 | 3/2003 | Singer |
| 6,544,732 | B1 | 4/2003 | Chee |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,737,236 | B1 | 5/2004 | Pieken et al. |
| 6,770,441 | B2 | 8/2004 | Dickinson |
| 6,773,886 | B2 | 8/2004 | Kaufman |
| 6,787,308 | B2 | 9/2004 | Balasubramanian |
| 6,797,470 | B2 | 9/2004 | Barany et al. |
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,499,806 | B2 | 3/2009 | Kermani et al. |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |
| 8,785,353 | B2 | 7/2014 | Van Eijk |
| 8,790,873 | B2 | 7/2014 | Namsaraev et al. |
| 8,809,238 | B2 | 8/2014 | Livak et al. |
| 8,815,512 | B2 | 8/2014 | Van Eijk |
| 8,835,358 | B2 | 9/2014 | Fodor |
| 8,865,410 | B2 | 10/2014 | Shendure |
| 8,906,626 | B2 | 12/2014 | Oliphant et al. |
| 8,911,945 | B2 | 12/2014 | Van Eijk |
| 8,936,912 | B2 | 1/2015 | Mitra |
| 8,951,726 | B2 | 2/2015 | Luo et al. |
| 8,951,728 | B2 | 2/2015 | Rasmussen |
| 8,986,926 | B2 | 3/2015 | Ferree et al. |
| 9,005,891 | B2 | 4/2015 | Sinicropi et al. |
| 9,005,935 | B2 | 4/2015 | Belyaev |
| 9,023,768 | B2 | 5/2015 | Van Eijk |
| 9,062,348 | B1 | 6/2015 | Van Eijk |
| 9,080,210 | B2 | 7/2015 | Van Eijk |
| 9,194,001 | B2 | 11/2015 | Brenner |
| 9,201,063 | B2 | 12/2015 | Sood et al. |
| 9,273,349 | B2 | 3/2016 | Nguyen et al. |
| 9,290,808 | B2 | 3/2016 | Fodor |
| 9,290,809 | B2 | 3/2016 | Fodor |
| 9,328,383 | B2 | 5/2016 | Van Eijk |
| 9,330,295 | B2 | 5/2016 | Dunn |
| 9,334,536 | B2 | 5/2016 | Van Eijk |
| 9,371,563 | B2 | 6/2016 | Geiss et al. |

(56) References Cited

U.S. PATENT DOCUMENTS 9,371,598 B2 6/2016 Chee
9,376,716 B2 6/2016 Van Eijk
9,376,717 B2 6/2016 Gao et al.
9,376,719 B2 6/2016 Eijk
9,416,409 B2 8/2016 Hayden
9,447,459 B2 9/2016 Van Eijk
9,453,256 B2 9/2016 Van Eijk
9,493,820 B2 11/2016 Van Eijk
9,506,061 B2 11/2016 Brown et al.
9,512,422 B2 12/2016 Barnard et al.
9,574,230 B2 2/2017 Van Eijk
9,593,365 B2 3/2017 Frisen et al.
9,598,728 B2 3/2017 Barany et al.
9,624,538 B2 4/2017 Church et al.
9,644,204 B2 5/2017 Hindson et al.
9,657,335 B2 5/2017 Van Eijk
9,670,542 B2 6/2017 Eijk
9,694,361 B2 7/2017 Bharadwaj
9,702,004 B2 7/2017 Van Eijk
9,714,446 B2 7/2017 Webster et al.
9,714,937 B2 7/2017 Dunaway
9,727,810 B2 8/2017 Fodor et al.
9,745,627 B2 8/2017 Van Eijk
9,777,324 B2 10/2017 Van Eijk
9,783,841 B2 10/2017 Nolan et al.
9,790,476 B2 10/2017 Gloeckner et al.
9,816,134 B2 11/2017 Namsaraev
9,834,814 B2 12/2017 Peter et al.
9,850,536 B2 12/2017 Oliphant et al.
9,856,521 B2 1/2018 Stevens et al.
9,868,979 B2 1/2018 Chee et al.
9,879,313 B2 1/2018 Chee et al.
9,896,721 B2 2/2018 Van Eijk
9,898,576 B2 2/2018 Van Eijk
9,898,577 B2 2/2018 Van Eijk
9,902,991 B2 2/2018 Sinicropi et al.
9,909,167 B2 3/2018 Samusik et al.
9,938,566 B2 4/2018 Shepard et al.
9,957,550 B2 5/2018 Yeakley et al.
10,002,316 B2 6/2018 Fodor et al.
10,023,907 B2 7/2018 Van Eijk
10,030,261 B2 7/2018 Frisen et al.
10,035,992 B2 7/2018 Gloeckner et al.
10,041,949 B2 8/2018 Bendall et al.
10,059,989 B2 8/2018 Giresi et al.
10,059,990 B2 8/2018 Boyden et al.
10,095,832 B2 10/2018 Van Eijk
10,101,336 B2 10/2018 Bergo
10,144,966 B2 12/2018 Cantor
10,208,982 B2 2/2019 Bannish et al.
10,227,639 B2 3/2019 Levner et al.
10,273,541 B2 4/2019 Hindson et al.
10,308,982 B2 6/2019 Chee
10,357,771 B2 7/2019 Bharadwaj
10,370,698 B2 8/2019 Nolan et al.
10,415,080 B2 9/2019 Dunaway et al.
10,465,235 B2 11/2019 Gullberg et al.
10,472,669 B2 11/2019 Chee
10,480,022 B2 11/2019 Chee
10,480,029 B2 11/2019 Bent et al.
10,494,667 B2 12/2019 Chee
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,544,403 B2 1/2020 Gloeckner et al.
10,550,429 B2 2/2020 Harada et al.
10,590,244 B2 3/2020 Delaney et al.
10,633,648 B2 4/2020 Seelig et al.
10,640,816 B2 5/2020 Beechem et al.
10,640,826 B2 5/2020 Church et al.
10,662,466 B2 5/2020 Berry et al.
10,662,468 B2 5/2020 Chee
10,669,569 B2 6/2020 Gullberg et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,815,519 B2 10/2020 Husain et al.
10,829,803 B2 11/2020 Terbrueggen et al.
10,844,426 B2 11/2020 Daugharthy et al.
10,858,698 B2 12/2020 Church et al.
10,858,702 B2 12/2020 Lucero et al.
10,913,975 B2 2/2021 So et al.
10,914,730 B2 2/2021 Chee et al.
10,927,403 B2 2/2021 Chee et al.
10,961,566 B2 3/2021 Chee
11,001,879 B1 5/2021 Chee
11,008,607 B2 5/2021 Chee
11,046,996 B1 6/2021 Chee et al.
11,067,567 B2 7/2021 Chee
11,104,936 B2 8/2021 Zhang et al.
11,118,216 B2 9/2021 Koshinsky et al.
11,156,603 B2 10/2021 Chee
11,162,132 B2 11/2021 Frisen et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,713,480 B2 8/2023 Lee
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.

(56) References Cited

U.S. PATENT DOCUMENTS 11,753,675 B2 9/2023 Ramachandran Iyer
11,761,030 B2 9/2023 Chee
11,761,038 B1 9/2023 Stoeckius
11,767,550 B2 9/2023 Chee
11,768,175 B1 9/2023 Kim et al.
11,773,433 B2 10/2023 Gallant et al.
11,781,130 B2 10/2023 Dadhwal
11,788,122 B2 10/2023 Frisen et al.
11,795,498 B2 10/2023 Frisen et al.
11,795,507 B2 10/2023 Chell et al.
11,808,769 B2 11/2023 Uytingco et al.
11,821,024 B2 11/2023 Chee et al.
11,821,035 B1 11/2023 Bent et al.
11,827,935 B1 11/2023 Ramachandran Iyer et al.
11,835,462 B2 12/2023 Bava
11,840,687 B2 12/2023 Gallant et al.
11,840,724 B2 12/2023 Chew et al.
11,845,979 B2 12/2023 Engblom et al.
11,859,178 B2 1/2024 Gallant et al.
11,866,767 B2 1/2024 Uytingco et al.
11,866,770 B2 1/2024 Chee
11,873,482 B2 1/2024 Kim et al.
11,891,654 B2 2/2024 Alvarado Martinez et al.
11,898,205 B2 2/2024 Bava
11,926,822 B1 3/2024 Gohil et al.
11,926,863 B1 3/2024 Boutet
11,926,867 B2 3/2024 Yin et al.
11,933,957 B1 3/2024 Tentori et al.
11,952,627 B2 4/2024 Stoeckius
11,959,076 B2 4/2024 Kim et al.
11,959,130 B2 4/2024 Galonska et al.
11,965,213 B2 4/2024 Williams
11,970,739 B2 4/2024 Chew et al.
11,981,958 B1 5/2024 Galonska
11,981,960 B1 5/2024 Lin et al.
11,981,965 B2 5/2024 Chell et al.
RE50,065 E 7/2024 Frisen et al.
12,024,741 B2 7/2024 Tentori et al.
12,031,177 B1 7/2024 Tentori et al.
12,060,604 B2 8/2024 Katiraee et al.
12,071,655 B2 8/2024 Sukovich et al.
12,076,701 B2 9/2024 Bava
12,098,417 B2 9/2024 Engblom et al.
12,098,985 B2 9/2024 Cox et al.
12,110,541 B2 10/2024 Bava
12,117,439 B2 10/2024 Delaney et al.
12,128,403 B2 10/2024 Kim et al.
12,129,516 B2 10/2024 Tentori et al.
12,157,124 B2 12/2024 Cox et al.
12,180,543 B2 12/2024 Uytingco et al.
12,195,790 B2 1/2025 Sukovich et al.
12,203,134 B2 1/2025 Nagendran et al.
12,209,280 B1 1/2025 Mignardi et al.
12,223,751 B2 2/2025 Li et al.
12,228,544 B2 2/2025 Kim et al.
12,234,505 B2 2/2025 Chee
12,241,060 B2 3/2025 Kim et al.
12,241,890 B2 3/2025 Delaney et al.
12,249,085 B2 3/2025 Tentori et al.
12,265,079 B1 4/2025 Bent
12,270,077 B2 4/2025 Schnall-Levin et al.
12,275,988 B2 4/2025 Galonska et al.
12,281,357 B1 4/2025 Tentori et al.
12,286,673 B2 4/2025 Bava
12,287,264 B2 4/2025 Cox et al.
12,297,486 B2 5/2025 Patterson et al.
12,297,487 B2 5/2025 Chee
12,297,488 B2 5/2025 Chee
12,344,892 B2 7/2025 Schnall-Levin et al.
12,365,935 B2 7/2025 Chew et al.
12,365,942 B2 7/2025 Stoeckius
12,371,688 B2 7/2025 Kim et al.
12,378,607 B2 8/2025 Schnall-Levin et al.
12,385,083 B2 8/2025 Shah
12,391,979 B2 8/2025 Chee
12,391,980 B2 8/2025 Chee
12,399,123 B1 8/2025 Shah et al.
12,404,544 B2 9/2025 Tentori et al.
12,405,264 B2 9/2025 Stoeckius
12,416,603 B2 9/2025 Tentori et al.
12,435,363 B1 10/2025 Gallant et al.
12,442,045 B2 10/2025 Williams
12,497,654 B2 12/2025 Ramachandran Iyer et al.
12,508,590 B2 12/2025 Kim et al.
D1,108,656 S 1/2026 Alimsijah et al.
12,529,094 B2 1/2026 Bent et al.
12,545,949 B2 2/2026 Bent et al.
12,553,805 B2 2/2026 Shahjamali
12,553,898 B1 2/2026 Uytingco et al.
12,566,113 B2 3/2026 Delaney et al.
12,566,114 B2 3/2026 Cox et al.
12,571,029 B1 3/2026 Galonska et al.
2001/0055764 A1 12/2001 Empendocles et al.
2002/0040275 A1 4/2002 Cravatt
2002/0051986 A1 5/2002 Baez et al.
2002/0055100 A1 5/2002 Kawashima
2002/0058250 A1 5/2002 Firth
2002/0086441 A1 7/2002 Baranov et al.
2002/0164611 A1 11/2002 Bamdad
2003/0017451 A1 1/2003 Wang et al.
2003/0022207 A1 1/2003 Balasubramanian
2003/0064398 A1 4/2003 Barnes
2003/0092624 A1 5/2003 Wang et al.
2003/0138879 A1 7/2003 Lambalot
2003/0148335 A1 8/2003 Shen et al.
2003/0162216 A1 8/2003 Gold
2003/0165948 A1 9/2003 Alsmadi et al.
2003/0211489 A1 11/2003 Shen et al.
2003/0224419 A1 12/2003 Corcoran
2003/0232348 A1 12/2003 Jones et al.
2003/0232382 A1 12/2003 Brennan
2003/0235854 A1 12/2003 Chan et al.
2004/0009487 A1 1/2004 Kadushin et al.
2004/0033499 A1 2/2004 Ilsley et al.
2004/0067492 A1 4/2004 Peng et al.
2004/0082059 A1 4/2004 Webb et al.
2004/0096853 A1 5/2004 Mayer
2004/0101835 A1 5/2004 Willis et al.
2004/0106110 A1 6/2004 Balasubramanian
2004/0235103 A1 11/2004 Reznikoff et al.
2004/0241660 A1 12/2004 Wojtowicz et al.
2004/0248325 A1 12/2004 Bukusoglu et al.
2004/0259105 A1 12/2004 Fan et al.
2005/0003431 A1 1/2005 Wucherpfennig
2005/0014203 A1 1/2005 Darfler et al.
2005/0037393 A1 2/2005 Gunderson et al.
2005/0048498 A1 3/2005 Woudenberg et al.
2005/0048580 A1 3/2005 Labaer
2005/0064460 A1 3/2005 Holliger et al.
2005/0095627 A1 5/2005 Kolman et al.
2005/0100900 A1 5/2005 Kawashima et al.
2005/0130173 A1 6/2005 Leamon et al.
2005/0136414 A1 6/2005 Gunderson et al.
2005/0164292 A1 7/2005 Farooqui
2005/0170373 A1 8/2005 Monforte
2005/0191656 A1 9/2005 Drmanac et al.
2005/0191698 A1 9/2005 Chee et al.
2005/0202433 A1 9/2005 Van Beuningen
2005/0227271 A1 10/2005 Kwon
2005/0239119 A1 10/2005 Tsukada et al.
2005/0260653 A1 11/2005 LaBaer
2005/0266417 A1 12/2005 Barany et al.
2006/0041385 A1 2/2006 Bauer et al.
2006/0046313 A1 3/2006 Roth
2006/0084078 A1 4/2006 Zhao
2006/0105352 A1 5/2006 Qiao et al.
2006/0154286 A1 7/2006 Kong et al.
2006/0188901 A1 8/2006 Barnes et al.
2006/0199183 A1 9/2006 Valat et al.
2006/0211001 A1 9/2006 Yu et al.
2006/0216775 A1 9/2006 Burkart et al.
2006/0240439 A1 10/2006 Smith et al.
2006/0263789 A1 11/2006 Kincaid
2006/0275782 A1 12/2006 Gunderson et al.

(56) References Cited

U.S. PATENT DOCUMENTS

2006/0281109 A1 12/2006 Barr Ost et al.
2007/0020640 A1 1/2007 McCloskey et al.
2007/0020669 A1 1/2007 Ericsson
2007/0026430 A1 2/2007 Andersen et al.
2007/0054288 A1 3/2007 Su et al.
2007/0087360 A1 4/2007 Boyd
2007/0099208 A1 5/2007 Drmanac et al.
2007/0128624 A1 6/2007 Gormley et al.
2007/0128656 A1 6/2007 Agrawal
2007/0134723 A1 6/2007 Kozlov et al.
2007/0161020 A1 7/2007 Luo et al.
2007/0166705 A1 7/2007 Milton et al.
2007/0172873 A1 7/2007 Brenner et al.
2007/0207482 A1 9/2007 Church et al.
2007/0254305 A1 11/2007 Paik et al.
2007/0269805 A1 11/2007 Hogers
2008/0003586 A1 1/2008 Hyde et al.
2008/0009420 A1 1/2008 Schroth et al.
2008/0108082 A1 5/2008 Rank et al.
2008/0108804 A1 5/2008 Hayashizaki et al.
2008/0132429 A1 6/2008 Perov et al.
2008/0160580 A1 7/2008 Adessi et al.
2008/0220434 A1 9/2008 Thomas
2008/0261204 A1 10/2008 Lexow
2008/0286795 A1 11/2008 Kawashima et al.
2008/0293046 A1 11/2008 Allawi et al.
2009/0005252 A1 1/2009 Drmanac et al.
2009/0006002 A1 1/2009 Honisch et al.
2009/0018024 A1 1/2009 Church et al.
2009/0026082 A1 1/2009 Rothberg et al.
2009/0036323 A1 2/2009 van Eijk et al.
2009/0082212 A1 3/2009 Williams
2009/0099041 A1 4/2009 Church et al.
2009/0105959 A1 4/2009 Braverman et al.
2009/0117573 A1 5/2009 Fu et al.
2009/0127589 A1 5/2009 Rothberg et al.
2009/0155781 A1 6/2009 Drmanac et al.
2009/0170713 A1 7/2009 van Eijk et al.
2009/0202998 A1 8/2009 Schlumpberger et al.
2009/0233802 A1 9/2009 Bignell et al.
2009/0253581 A1 10/2009 van Eijk et al.
2009/0270273 A1 10/2009 Burns et al.
2009/0283407 A1 11/2009 Van Eijk
2009/0286249 A1 11/2009 Becker et al.
2009/0291854 A1 11/2009 Weisinger-Mayr et al.
2009/0312193 A1 12/2009 Kim et al.
2010/0035249 A1 2/2010 Hayashizaki et al.
2010/0047790 A1 2/2010 Southern et al.
2010/0069263 A1 3/2010 Shendure et al.
2010/0105052 A1 4/2010 Drmanac et al.
2010/0120097 A1 5/2010 Matz et al.
2010/0120098 A1 5/2010 Grunenwald et al.
2010/0129874 A1 5/2010 Mitra et al.
2010/0145037 A1 6/2010 Brive et al.
2010/0173384 A1 7/2010 Johnsson et al.
2010/0184618 A1 7/2010 Namsaraev et al.
2010/0210475 A1 8/2010 Lee et al.
2010/0227329 A1 9/2010 Cuppens
2010/0273219 A1 10/2010 May et al.
2010/0273679 A1 10/2010 Cuppoletti et al.
2011/0028685 A1 2/2011 Purkayastha et al.
2011/0031123 A1 2/2011 Schulze et al.
2011/0033854 A1 2/2011 Drmanac et al.
2011/0045462 A1 2/2011 Fu et al.
2011/0059436 A1 3/2011 Hardin et al.
2011/0111409 A1 5/2011 Sinicropi et al.
2011/0152111 A1 6/2011 Fan et al.
2011/0237449 A1 9/2011 McMaster et al.
2011/0245101 A1 10/2011 Chee et al.
2011/0245111 A1 10/2011 Chee
2011/0269631 A1 11/2011 Fu et al.
2011/0287435 A1 11/2011 Grunenwald et al.
2012/0010091 A1 1/2012 Linnarson
2012/0021930 A1 1/2012 Schoen et al.
2012/0046175 A1 2/2012 Rodesch et al.
2012/0046178 A1 2/2012 Van Den Boom et al.
2012/0065081 A1 3/2012 Chee
2012/0135871 A1 5/2012 van Eijk et al.
2012/0202698 A1 8/2012 van Eijk et al.
2012/0202704 A1 8/2012 Fan et al.
2012/0220479 A1 8/2012 Ericsson et al.
2012/0245053 A1 9/2012 Shirai et al.
2012/0252702 A1 10/2012 Muratani et al.
2012/0258871 A1 10/2012 Kozlov et al.
2012/0289414 A1 11/2012 Mitra et al.
2012/0301925 A1 11/2012 Belyaev
2013/0005594 A1 1/2013 Terbrueggen et al.
2013/0005600 A1 1/2013 Olek
2013/0023433 A1 1/2013 Luo et al.
2013/0035239 A1 2/2013 Kong et al.
2013/0040842 A1 2/2013 Lim et al.
2013/0065768 A1 3/2013 Zheng et al.
2013/0079232 A1 3/2013 Kain et al.
2013/0171621 A1 7/2013 Luo et al.
2013/0244884 A1 9/2013 Jacobson et al.
2013/0261019 A1 10/2013 Lin et al.
2013/0302801 A1 11/2013 Asbury et al.
2013/0338042 A1 12/2013 Shen et al.
2014/0066318 A1 3/2014 Frisen et al.
2014/0121118 A1 5/2014 Warner
2014/0270435 A1 9/2014 Dunn
2014/0274731 A1 9/2014 Raymond et al.
2014/0323330 A1 10/2014 Glezer et al.
2014/0342921 A1 11/2014 Weiner
2014/0378350 A1 12/2014 Hindson et al.
2015/0000854 A1 1/2015 Gann-Fetter et al.
2015/0292988 A1 10/2015 Bharadwaj et al.
2015/0344942 A1 12/2015 Frisen et al.
2016/0019337 A1 1/2016 Roberts et al.
2016/0024576 A1 1/2016 Chee
2016/0041159 A1 2/2016 Labaer et al.
2016/0060687 A1 3/2016 Zhu et al.
2016/0108458 A1 4/2016 Frei et al.
2016/0122817 A1 5/2016 Jarosz et al.
2016/0138091 A1 5/2016 Chee et al.
2016/0145677 A1 5/2016 Chee et al.
2016/0194692 A1 7/2016 Gore et al.
2016/0201125 A1 7/2016 Samuels et al.
2016/0253584 A1 9/2016 Fodor et al.
2016/0289740 A1 10/2016 Fu et al.
2016/0298180 A1 10/2016 Chee
2016/0305856 A1 10/2016 Boyden et al.
2016/0312276 A1 10/2016 Fu et al.
2016/0333403 A1 11/2016 Chee
2016/0376642 A1 12/2016 Landegren et al.
2017/0009278 A1 1/2017 Söderberg et al.
2017/0016053 A1 1/2017 Beechem et al.
2017/0029875 A1 2/2017 Zhang et al.
2017/0058339 A1 3/2017 Chee
2017/0058340 A1 3/2017 Chee
2017/0058345 A1 3/2017 Chee
2017/0067096 A1 3/2017 Wassie et al.
2017/0088881 A1 3/2017 Chee
2017/0089811 A1 3/2017 Tillberg et al.
2017/0159109 A1 6/2017 Zheng et al.
2017/0166962 A1 6/2017 van Eijk et al.
2017/0220733 A1 8/2017 Zhuang et al.
2017/0233722 A1 8/2017 Seelig et al.
2017/0241911 A1 8/2017 Rockel et al.
2017/0283860 A1 10/2017 Kool et al.
2017/0335297 A1 11/2017 Ha et al.
2017/0335410 A1 11/2017 Driscoll et al.
2017/0342405 A1 11/2017 Fu et al.
2017/0349940 A1 12/2017 Morin et al.
2018/0051322 A1 2/2018 Church et al.
2018/0057873 A1 3/2018 Zhou et al.
2018/0080019 A1 3/2018 Blainey et al.
2018/0088112 A1 3/2018 Fan et al.
2018/0094316 A1 4/2018 Oliphant et al.
2018/0112261 A1 4/2018 Van Driel et al.
2018/0127817 A1 5/2018 Borchert et al.
2018/0163265 A1 6/2018 Zhang et al.
2018/0179591 A1 6/2018 van Eijk
2018/0201925 A1 7/2018 Steemers et al.

(56) References Cited

U.S. PATENT DOCUMENTS

| | | | |
|---|---|---|---|
| 2018/0201980 | A1 | 7/2018 | Chee et al. |
| 2018/0208967 | A1 | 7/2018 | Larman et al. |
| 2018/0216161 | A1 | 8/2018 | Chen et al. |
| 2018/0216162 | A1 | 8/2018 | Belhocine et al. |
| 2018/0237864 | A1 | 8/2018 | Imler et al. |
| 2018/0245142 | A1 | 8/2018 | So et al. |
| 2018/0247017 | A1 | 8/2018 | van Eijk et al. |
| 2018/0291427 | A1 | 10/2018 | Edelman |
| 2018/0291439 | A1 | 10/2018 | van Eijk et al. |
| 2018/0305681 | A1 | 10/2018 | Jovanovich et al. |
| 2018/0312822 | A1 | 11/2018 | Lee et al. |
| 2018/0320226 | A1 | 11/2018 | Church et al. |
| 2018/0334670 | A1 | 11/2018 | Bharadwaj et al. |
| 2019/0055594 | A1 | 2/2019 | Samusik et al. |
| 2019/0064173 | A1 | 2/2019 | Bharadwaj et al. |
| 2019/0071656 | A1 | 3/2019 | Chang et al. |
| 2019/0085383 | A1 | 3/2019 | Church et al. |
| 2019/0119735 | A1 | 4/2019 | Deisseroth et al. |
| 2019/0135774 | A1 | 5/2019 | Orbai |
| 2019/0145982 | A1 | 5/2019 | Chee et al. |
| 2019/0161796 | A1 | 5/2019 | Hauling et al. |
| 2019/0177777 | A1 | 6/2019 | Chee |
| 2019/0177778 | A1 | 6/2019 | Chee |
| 2019/0177789 | A1 | 6/2019 | Hindson et al. |
| 2019/0177800 | A1 | 6/2019 | Boutet et al. |
| 2019/0194709 | A1 | 6/2019 | Church et al. |
| 2019/0203275 | A1 | 7/2019 | Frisen et al. |
| 2019/0218276 | A1 | 7/2019 | Regev et al. |
| 2019/0218608 | A1 | 7/2019 | Daugharthy et al. |
| 2019/0233878 | A1 | 8/2019 | Delaney et al. |
| 2019/0233880 | A1 | 8/2019 | Mir |
| 2019/0249226 | A1 | 8/2019 | Bent et al. |
| 2019/0262831 | A1 | 8/2019 | West et al. |
| 2019/0264268 | A1 | 8/2019 | Frisen et al. |
| 2019/0271028 | A1 | 9/2019 | Khafizov et al. |
| 2019/0271030 | A1 | 9/2019 | Chee |
| 2019/0271031 | A1 | 9/2019 | Chee |
| 2019/0300943 | A1 | 10/2019 | Chee et al. |
| 2019/0300944 | A1 | 10/2019 | Chee et al. |
| 2019/0300945 | A1 | 10/2019 | Chee et al. |
| 2019/0309353 | A1 | 10/2019 | Chee |
| 2019/0309354 | A1 | 10/2019 | Chee |
| 2019/0309355 | A1 | 10/2019 | Chee |
| 2019/0323071 | A1 | 10/2019 | Chee |
| 2019/0323088 | A1 | 10/2019 | Boutet et al. |
| 2019/0330617 | A1 | 10/2019 | Church et al. |
| 2019/0338353 | A1 | 11/2019 | Belgrader et al. |
| 2019/0360034 | A1 | 11/2019 | Zhou et al. |
| 2019/0360043 | A1 | 11/2019 | Pham et al. |
| 2019/0367969 | A1 | 12/2019 | Belhocine et al. |
| 2019/0367982 | A1 | 12/2019 | Belhocine et al. |
| 2019/0367997 | A1 | 12/2019 | Bent et al. |
| 2020/0002763 | A1 | 1/2020 | Belgrader et al. |
| 2020/0010891 | A1 | 1/2020 | Beechem et al. |
| 2020/0024641 | A1 | 1/2020 | Nolan et al. |
| 2020/0040376 | A1 | 2/2020 | Russel et al. |
| 2020/0047010 | A1 | 2/2020 | Lee et al. |
| 2020/0048690 | A1 | 2/2020 | Chee |
| 2020/0063191 | A1 | 2/2020 | Kennedy-Darling et al. |
| 2020/0063195 | A1 | 2/2020 | Chee |
| 2020/0063196 | A1 | 2/2020 | Chee |
| 2020/0071751 | A1 | 3/2020 | Daugharthy et al. |
| 2020/0080136 | A1 | 3/2020 | Zhang et al. |
| 2020/0109443 | A1 | 4/2020 | Chee |
| 2020/0123597 | A1 | 4/2020 | Daniel |
| 2020/0131570 | A1 | 4/2020 | Berti et al. |
| 2020/0140920 | A1 | 5/2020 | Pierce et al. |
| 2020/0173985 | A1 | 6/2020 | Dong et al. |
| 2020/0199565 | A1 | 6/2020 | Chen et al. |
| 2020/0199572 | A1 | 6/2020 | Kuersten et al. |
| 2020/0224244 | A1 | 7/2020 | Nilsson et al. |
| 2020/0239874 | A1 | 7/2020 | Mikkelsen |
| 2020/0239946 | A1 | 7/2020 | Dewal |
| 2020/0256867 | A1 | 8/2020 | Hennek et al. |
| 2020/0277663 | A1 | 9/2020 | Iyer |
| 2020/0277664 | A1 | 9/2020 | Frenz |
| 2020/0283852 | A1 | 9/2020 | Oliphant et al. |
| 2020/0299757 | A1 | 9/2020 | Chee et al. |
| 2020/0325531 | A1 | 10/2020 | Chee |
| 2020/0362398 | A1 | 11/2020 | Kishi et al. |
| 2020/0370095 | A1 | 11/2020 | Farmer et al. |
| 2020/0399687 | A1 | 12/2020 | Frisen et al. |
| 2020/0407781 | A1 | 12/2020 | Schnall-Levin |
| 2021/0010068 | A1 | 1/2021 | Chee et al. |
| 2021/0010070 | A1 | 1/2021 | Schnall-Levin et al. |
| 2021/0017587 | A1 | 1/2021 | Cai et al. |
| 2021/0095331 | A1 | 4/2021 | Fan et al. |
| 2021/0115504 | A1 | 4/2021 | Cai et al. |
| 2021/0123040 | A1 | 4/2021 | Macosko et al. |
| 2021/0130881 | A1 | 5/2021 | Cox |
| 2021/0140982 | A1 | 5/2021 | Uytingco et al. |
| 2021/0155982 | A1 | 5/2021 | Yin et al. |
| 2021/0158522 | A1 | 5/2021 | Weisenfeld et al. |
| 2021/0172007 | A1 | 6/2021 | Chee et al. |
| 2021/0189475 | A1 | 6/2021 | Tentori et al. |
| 2021/0190770 | A1 | 6/2021 | Delaney et al. |
| 2021/0198741 | A1 | 7/2021 | Williams |
| 2021/0199660 | A1 | 7/2021 | Williams et al. |
| 2021/0207202 | A1 | 7/2021 | Chee |
| 2021/0214785 | A1 | 7/2021 | Stoeckius |
| 2021/0222235 | A1 | 7/2021 | Chee |
| 2021/0222241 | A1 | 7/2021 | Bharadwaj |
| 2021/0222242 | A1 | 7/2021 | Ramachandran Iyer |
| 2021/0222253 | A1 | 7/2021 | Uytingco |
| 2021/0223227 | A1 | 7/2021 | Stoeckius |
| 2021/0230584 | A1 | 7/2021 | Mikkelsen et al. |
| 2021/0230681 | A1 | 7/2021 | Patterson et al. |
| 2021/0230692 | A1 | 7/2021 | Daugharthy et al. |
| 2021/0237022 | A1 | 8/2021 | Bava |
| 2021/0238581 | A1 | 8/2021 | Mikkelsen et al. |
| 2021/0238664 | A1 | 8/2021 | Bava et al. |
| 2021/0238675 | A1 | 8/2021 | Bava |
| 2021/0238680 | A1 | 8/2021 | Bava |
| 2021/0247316 | A1 | 8/2021 | Bava |
| 2021/0255175 | A1 | 8/2021 | Chee et al. |
| 2021/0262018 | A1 | 8/2021 | Bava et al. |
| 2021/0262019 | A1 | 8/2021 | Alvarado Martinez et al. |
| 2021/0269864 | A1 | 9/2021 | Chee |
| 2021/0270822 | A1 | 9/2021 | Chee |
| 2021/0277460 | A1 | 9/2021 | Bava |
| 2021/0285036 | A1 | 9/2021 | Yin et al. |
| 2021/0285046 | A1 | 9/2021 | Chell et al. |
| 2021/0292748 | A1 | 9/2021 | Frisen et al. |
| 2021/0292822 | A1 | 9/2021 | Frisen et al. |
| 2021/0317510 | A1 | 10/2021 | Chee et al. |
| 2021/0317524 | A1 | 10/2021 | Lucero et al. |
| 2021/0324457 | A1 | 10/2021 | Ramachandran Iyer et al. |
| 2021/0332424 | A1 | 10/2021 | Schnall-Levin |
| 2021/0332425 | A1 | 10/2021 | Pfeiffer et al. |
| 2021/0348221 | A1 | 11/2021 | Chell et al. |
| 2022/0002791 | A1 | 1/2022 | Frisen et al. |
| 2022/0003755 | A1 | 1/2022 | Chee |
| 2022/0010367 | A1 | 1/2022 | Ramachandran Iyer et al. |
| 2022/0017951 | A1 | 1/2022 | Ramachandran Iyer et al. |
| 2022/0025446 | A1 | 1/2022 | Shah |
| 2022/0025447 | A1 | 1/2022 | Tentori et al. |
| 2022/0033888 | A1 | 2/2022 | Schnall-Levin et al. |
| 2022/0049293 | A1 | 2/2022 | Frenz et al. |
| 2022/0064630 | A1 | 3/2022 | Bent et al. |
| 2022/0081728 | A1 | 3/2022 | Williams |
| 2022/0090058 | A1 | 3/2022 | Frisen et al. |
| 2022/0090175 | A1 | 3/2022 | Uytingco et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |

(56) References Cited

U.S. PATENT DOCUMENTS

| | | | |
|---|---|---|---|
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0220544 | A1 | 7/2022 | Ach et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0315984 | A1 | 10/2022 | Edelman et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0334031 | A1 | 10/2022 | Delaney et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |
| 2022/0364163 | A1 | 11/2022 | Stahl et al. |
| 2022/0389491 | A1 | 12/2022 | Chee |
| 2022/0389503 | A1 | 12/2022 | Mikkelsen et al. |
| 2022/0389504 | A1 | 12/2022 | Chew et al. |
| 2022/0403374 | A1 | 12/2022 | Soumillon |
| 2022/0403455 | A1 | 12/2022 | Ramachandran Iyer et al. |
| 2022/0404245 | A1 | 12/2022 | Chell et al. |
| 2023/0002812 | A1 | 1/2023 | Stoeckius et al. |
| 2023/0014008 | A1 | 1/2023 | Shastry |
| 2023/0017773 | A1 | 1/2023 | Kim et al. |
| 2023/0031305 | A1 | 2/2023 | Hernandez Neuta et al. |
| 2023/0033960 | A1 | 2/2023 | Gallant et al. |
| 2023/0034039 | A1 | 2/2023 | Shahjamali |
| 2023/0034216 | A1 | 2/2023 | Bava |
| 2023/0040363 | A1 | 2/2023 | Chee |
| 2023/0042088 | A1 | 2/2023 | Chee |
| 2023/0042817 | A1 | 2/2023 | Mignardi |
| 2023/0047782 | A1 | 2/2023 | Tentori et al. |
| 2023/0056549 | A1 | 2/2023 | Dadhwal |
| 2023/0064372 | A1 | 3/2023 | Chell et al. |
| 2023/0069046 | A1 | 3/2023 | Chew et al. |
| 2023/0077364 | A1 | 3/2023 | Patterson et al. |
| 2023/0080543 | A1 | 3/2023 | Katiraee et al. |
| 2023/0081381 | A1 | 3/2023 | Chew et al. |
| 2023/0100497 | A1 | 3/2023 | Frisen et al. |
| 2023/0107023 | A1 | 4/2023 | Chee |
| 2023/0111225 | A1 | 4/2023 | Chew et al. |
| 2023/0113230 | A1 | 4/2023 | Kim et al. |
| 2023/0126825 | A1 | 4/2023 | Nagendran et al. |
| 2023/0129552 | A1 | 4/2023 | Ramachandran Iyer |
| 2023/0135010 | A1 | 5/2023 | Tentori et al. |
| 2023/0143569 | A1 | 5/2023 | Iyer et al. |
| 2023/0145575 | A1 | 5/2023 | Gallant et al. |
| 2023/0147726 | A1 | 5/2023 | Hadrup et al. |
| 2023/0151412 | A1 | 5/2023 | Chee |
| 2023/0159994 | A1 | 5/2023 | Chee |
| 2023/0159995 | A1 | 5/2023 | Iyer et al. |
| 2023/0160008 | A1 | 5/2023 | Chell et al. |
| 2023/0175045 | A1 | 6/2023 | Katsori et al. |
| 2023/0183684 | A1 | 6/2023 | Gallant et al. |
| 2023/0183785 | A1 | 6/2023 | Frisen et al. |
| 2023/0194469 | A1 | 6/2023 | Tentori et al. |
| 2023/0194470 | A1 | 6/2023 | Kim et al. |
| 2023/0203478 | A1 | 6/2023 | Kim et al. |
| 2023/0212650 | A1 | 7/2023 | Chew et al. |
| 2023/0212655 | A1 | 7/2023 | Chee |
| 2023/0212656 | A1 | 7/2023 | Chow et al. |
| 2023/0220368 | A1 | 7/2023 | Kim |
| 2023/0220454 | A1 | 7/2023 | Bent et al. |
| 2023/0220455 | A1 | 7/2023 | Galonska et al. |
| 2023/0227811 | A1 | 7/2023 | Dadhwal |
| 2023/0228762 | A1 | 7/2023 | Uytingco et al. |
| 2023/0242973 | A1 | 8/2023 | Frisen et al. |
| 2023/0242976 | A1 | 8/2023 | Tentori et al. |
| 2023/0265488 | A1 | 8/2023 | Gohil et al. |
| 2023/0265489 | A1 | 8/2023 | Uytingco et al. |
| 2023/0265491 | A1 | 8/2023 | Tentori et al. |
| 2023/0267625 | A1 | 8/2023 | Tentori et al. |
| 2023/0279474 | A1 | 9/2023 | Katiraee |
| 2023/0279477 | A1 | 9/2023 | Kvastad et al. |
| 2023/0279481 | A1 | 9/2023 | Marrache et al. |
| 2023/0287399 | A1 | 9/2023 | Gallant et al. |
| 2023/0287475 | A1 | 9/2023 | Chell et al. |
| 2023/0287481 | A1 | 9/2023 | Katsori et al. |
| 2023/0295699 | A1 | 9/2023 | Sukovich et al. |
| 2023/0295722 | A1 | 9/2023 | Bharadwaj |
| 2023/0304072 | A1 | 9/2023 | Gohil et al. |
| 2023/0304074 | A1 | 9/2023 | Chee et al. |
| 2023/0304078 | A1 | 9/2023 | Frisen et al. |
| 2023/0313279 | A1 | 10/2023 | Giacomello et al. |
| 2023/0323340 | A1 | 10/2023 | Dadhwal |
| 2023/0323434 | A1 | 10/2023 | Yin et al. |
| 2023/0323436 | A1 | 10/2023 | Chee |
| 2023/0323447 | A1 | 10/2023 | Schnall-Levin et al. |
| 2023/0323453 | A1 | 10/2023 | Stoeckius |
| 2023/0332138 | A1 | 10/2023 | Kim et al. |
| 2023/0332211 | A1 | 10/2023 | Chee |
| 2023/0332212 | A1 | 10/2023 | Chew et al. |
| 2023/0332227 | A1 | 10/2023 | Ramachandran Iyer |
| 2023/0332247 | A1 | 10/2023 | Singh et al. |
| 2023/0351619 | A1 | 11/2023 | Tentori et al. |
| 2023/0358733 | A1 | 11/2023 | Chee |
| 2023/0366008 | A1 | 11/2023 | Chew et al. |
| 2023/0383285 | A1 | 11/2023 | Kim et al. |
| 2023/0383344 | A1 | 11/2023 | Stoeckius |
| 2023/0392204 | A1 | 12/2023 | Chell et al. |
| 2023/0393071 | A1 | 12/2023 | Bava |
| 2023/0407404 | A1 | 12/2023 | Baumgartner et al. |
| 2023/0416807 | A1 | 12/2023 | Chee |
| 2023/0416808 | A1 | 12/2023 | Sukovich et al. |
| 2023/0416850 | A1 | 12/2023 | Singh et al. |
| 2024/0002931 | A1 | 1/2024 | Bava |
| 2024/0011081 | A1 | 1/2024 | Chee |
| 2024/0011090 | A1 | 1/2024 | Chew et al. |
| 2024/0018572 | A1 | 1/2024 | Mignardi |
| 2024/0018575 | A1 | 1/2024 | Gallant et al. |
| 2024/0018589 | A1 | 1/2024 | Schnall-Levin et al. |
| 2024/0026445 | A1 | 1/2024 | Ramachandran Iyer et al. |
| 2024/0033743 | A1 | 2/2024 | Tentori et al. |
| 2024/0035937 | A1 | 2/2024 | Cox et al. |
| 2024/0043925 | A1 | 2/2024 | Bent et al. |
| 2024/0052343 | A1 | 2/2024 | Gallant et al. |
| 2024/0053351 | A1 | 2/2024 | Uytingco et al. |
| 2024/0060115 | A1 | 2/2024 | Chee et al. |
| 2024/0067953 | A1 | 2/2024 | Mikkelsen et al. |
| 2024/0068016 | A1 | 2/2024 | Frisen et al. |
| 2024/0068017 | A1 | 2/2024 | Lundeberg et al. |
| 2024/0076723 | A1 | 3/2024 | Mignardi |
| 2024/0080346 | A1 | 3/2024 | Engblom et al. |
| 2024/0084365 | A1 | 3/2024 | Frisen et al. |
| 2024/0084366 | A1 | 3/2024 | Chee |
| 2024/0084383 | A1 | 3/2024 | Ramachandran Iyer et al. |
| 2024/0093274 | A1 | 3/2024 | Frisen et al. |
| 2024/0093290 | A1 | 3/2024 | Stahl et al. |
| 2024/0110228 | A1 | 4/2024 | Uytingco et al. |
| 2024/0124933 | A1 | 4/2024 | Chell et al. |
| 2024/0125772 | A1 | 4/2024 | Delaney et al. |
| 2024/0141327 | A1 | 5/2024 | Kim et al. |
| 2024/0158838 | A1 | 5/2024 | Alvarado Martinez et al. |
| 2024/0175080 | A1 | 5/2024 | Galonska et al. |
| 2024/0182968 | A1 | 6/2024 | Bava |
| 2024/0191286 | A1 | 6/2024 | Boutet et al. |
| 2024/0200121 | A1 | 6/2024 | Boutet |
| 2024/0209425 | A1 | 6/2024 | Yin et al. |
| 2024/0218427 | A1 | 7/2024 | Sukovich et al. |
| 2024/0218432 | A1 | 7/2024 | Mielinis |
| 2024/0219701 | A1 | 7/2024 | Tentori et al. |
| 2024/0253036 | A1 | 8/2024 | Kim et al. |
| 2024/0263218 | A1 | 8/2024 | Katiraee et al. |
| 2024/0271190 | A1 | 8/2024 | Stoeckius et al. |
| 2024/0271195 | A1 | 8/2024 | Mikhaiel et al. |

(56) References Cited

U.S. PATENT DOCUMENTS

| | | | |
|---|---|---|---|
| 2024/0279712 | A1 | 8/2024 | Fan et al. |
| 2024/0279747 | A1 | 8/2024 | Williams |
| 2024/0287600 | A1 | 8/2024 | Iyer et al. |
| 2024/0294971 | A1 | 9/2024 | Galonska |
| 2024/0294974 | A1 | 9/2024 | Galonska et al. |
| 2024/0294975 | A1 | 9/2024 | Lin et al. |
| 2024/0301488 | A1 | 9/2024 | Stoeckius |
| 2024/0301489 | A1 | 9/2024 | Chew et al. |
| 2024/0360494 | A1 | 10/2024 | Costa et al. |
| 2024/0368711 | A1 | 11/2024 | Giacomello et al. |
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Ramachandran Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340932 | A1 | 11/2025 | Chee |
| 2025/0340933 | A1 | 11/2025 | Giacomello et al. |
| 2025/0354931 | A1 | 11/2025 | Shah et al. |
| 2025/0369037 | A1 | 12/2025 | Gupta |
| 2025/0376676 | A1 | 12/2025 | Kim et al. |
| 2025/0376719 | A1 | 12/2025 | Shah |
| 2025/0382665 | A1 | 12/2025 | Frenz et al. |
| 2026/0002202 | A1 | 1/2026 | Schnall-Levin et al. |
| 2026/0009784 | A1 | 1/2026 | Stoeckius |
| 2026/0015653 | A1 | 1/2026 | Chew et al. |
| 2026/0022419 | A1 | 1/2026 | Bent et al. |
| 2026/0035740 | A1 | 2/2026 | Chee |
| 2026/0049349 | A1 | 2/2026 | Gallant et al. |
| 2026/0055443 | A1 | 2/2026 | Tentori et al. |
| 2026/0071262 | A1 | 3/2026 | Yin et al. |
| 2026/0103754 | A1 | 4/2026 | Schnall-Levin et al. |
| 2026/0117286 | A1 | 4/2026 | Katiraee et al. |
| 2026/0117289 | A1 | 4/2026 | Kim |
| 2026/0117298 | A1 | 4/2026 | Doddridge |
| 2026/0117299 | A1 | 4/2026 | Kim et al. |
| 2026/0117302 | A1 | 4/2026 | Chell et al. |
| 2026/0124615 | A1 | 5/2026 | Kim et al. |
| 2026/0132449 | A1 | 5/2026 | Galonska et al. |
| 2026/0132451 | A1 | 5/2026 | Ramachandran Iyer et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |

(56) References Cited

FOREIGN PATENT DOCUMENTS

| | | |
|---|---|---|
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/019964 | 2/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/192292 | 12/2013 |
| WO | WO 2014/044724 | 3/2014 |
| WO | WO 2014/060483 | 4/2014 |
| WO | WO 2014/066179 | 5/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/057319 | 4/2015 |
| WO | WO 2015/069374 | 5/2015 |
| WO | WO 2015/094861 | 6/2015 |
| WO | WO 2015/122967 | 8/2015 |
| WO | WO 2015/161173 | 10/2015 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2018/217862 | 11/2018 |
| WO | WO 2019/023214 | 1/2019 |
| WO | WO 2019/032760 | 2/2019 |
| WO | WO 2019/068880 | 4/2019 |
| WO | WO 2019/089836 | 5/2019 |
| WO | WO 2019/089851 | 5/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/222523 | 11/2019 |
| WO | WO 2019/241290 | 12/2019 |
| WO | WO 2020/028194 | 2/2020 |
| WO | WO 2020/041148 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |

(56) References Cited

FOREIGN PATENT DOCUMENTS

| | | |
|---|---|---|
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

10xGenomics.com, [online], “Visium Spatial Gene Expression Reagent Kits—Tissue Optimization—User Guide,” Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.

10xGenomics.com, [online], “Visium Spatial Gene Expression Reagent Kits—User Guide,” Sep. 2023, retrieved on Mar. 29, 2024, retrieved from URL<https://cdn.10xgenomics.com/image/upload/v1695417753/support-documents/CG000239_VisiumSpatialGeneExpression_UserGuide_RevG.pdf>, 70 pages.

Asp et al., “A spatiotemporal organ-wide gene expression and cell atlas of the developing human heart,” Cell, Dec. 12, 2019, 179(7):1647-1660.

Kuhn et al., “A novel, high-performance random array platform for quantitative gene expression profiling,” Genome Res, 2004, 14:2347-2356.

PCT International Preliminary Report on Patentability in International Appln. No. PCT/US2022/042320, dated Mar. 14, 2024, 9 pages.

10xGenomics.com, [online], “Visium Spatial Gene Expression Reagent Kits—User Guide,” Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

[No Author Listed], “Chromium Next GEM Single Cell 3' Reagent Kits v3.1—User Guide,” 10x Genomics, Document No. CG000204, Nov. 2019, 58 pages.

[No Author Listed], “Chromium Next GEM Single Cell 3' Reagent Kits v3.1 (Dual Index)—User Guide,” 10x Genomics, Mar. 2021, Document No. CG000315, 61 pages.

[No Author Listed], “HuSNP Mapping Assay User’s Manual,” Affymetrix Part No. 90094 (Affymetrix, Santa Clara, Calif.), GeneChip, 2000, 104 pages.

[No Author Listed], “Microarray technologies have excellent possibilities in genomics-related researches,” Science Tools From Amersham Pharmacia Biotech, 1998, 3(4): 8 pages (with English Translation).

[No Author Listed], “Proseek® Multiplex 96×96 User Manual,” Olink Proteomics, Olink Bioscience, Uppsala, Sweden, 2017, 20 pages.

10xGenomics.com, [online], “Visium Spatial Gene Expression Reagent Kits—Tissue Optimization—User Guide,” Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.

10xGenomics.com, [online], “Visium Spatial Gene Expression Reagent Kits—Tissue Optimization,” Nov. 2019, retrieved on Jan. 25, 2022,

(56) References Cited

OTHER PUBLICATIONS retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal G.T Mismatches in DNA," Biochemistry, 1996, 36(34):10581-10594.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Andresen et al., "Helicase-dependent amplification: use in OnChip amplification and potential for point-of-care diagnostics," Expert Rev Mol Diagn., Oct. 2009, 9(7):645-650.

Appella, "Non-natural nucleic acids for synthetic biology," Current Opinion in Chemical Biology, Dec. 2009, 13(5-6): 687-696.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al, "2D-PCR: a method of mapping DNA in tissue sections," Lab Chip, 2009, 9(24):3526-34.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Asp et al., "Spatially Resolved Transcriptomes—Next Generation Tools for Tissue Exploration," Bioessays, Oct. 2020, 42(10):e1900221, 16 pages.

Atkinson et al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Balakrishnan et al., "Flap endonuclease 1," Annu Rev Biochem., Jun. 2013, 82:119-138.

Baner et al., "Signal amplification of padlock probes by rolling circle replication," Nucleic Acids Res., 1998, 26(22):5073-5078.

Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Bartosovic et al., "Single-cell CUT&Tag profiles histone modifications and transcription factors in complex tissues," Nat Biotechnol., Jul. 2021, 39(7):825-835, Abstract.

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.

Bell, "A simple way to treat PCR products prior to sequencing using ExoSAP-IT," Biotechniques, 2008, 44(6):834, 1 page.

Belton et al., "Hi-C: A comprehensive technique to capture the conformation of genomes," Methods, Nov. 2012, 58(3):268-276, 16 pages.

Bentley et al., "Accurate whole human genome sequencing using reversible terminator chemistry," Nature, 2008, 456(7218):53-59.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Bibikova et al., "Quantitative gene expression profiling in formalin-fixed paraffin-embedded tissues using universal bead arrays," The American Journal of Pathology, Nov. 1, 2004, 165(5):1799-1807.

Birney et al., "Identification and analysis of functional elements in 1% of the human genome by the ENCODE pilot project," Nature, 2007, 447(7146):799-816.

Blair et al., "Microarray temperature optimization using hybridization kinetics," Methods Mol Biol., 2009, 529:171-96.

Blanchard et al., "High-density oligonucleotide arrays," Biosensors & Bioelectronics, 1996, 11(6-7):687-690.

Blanco et al., "A practical approach to FRET-based PNA fluorescence in situ hybridization," Methods, Dec. 2010, 52(4):343-51.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolotin et al., "MiXCR: software for comprehensive adaptive immunity profiling," Nat Methods., May 2015, 12(5):380-1.

Borm et al., "High throughput human embryo spatial transcriptome mapping by surface transfer of tissue RNA," Abstracts Selected Talks, Single Cell Genomics mtg, (SCG2019), 2019, 1 pages (Abstract Only).

Boulé et al., "Terminal deoxynucleotidyl transferase indiscriminately incorporates ribonucleotides and deoxyribonucleotides," J Biol Chem., Aug. 2001, 276(33):31388-93.

Brandon et al., "Mitochondrial mutations in cancer," Oncogene, 2006, 25(34):4647-4662.

(56) References Cited

OTHER PUBLICATIONS

Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Cai et al., "Tenascin-c mediated vasculogenic mimicry formation via regulation of MMP2/MMP9 in glioma," Cell Death and Disease, Nov. 21, 2019, 10(879):1-14.
Caliari et al., "A practical guide to hydrogels for cell culture," Nat Methods., Apr. 2016, 13(5):405-14.
Cantata Bio, "Dovetail Micro-C Kit User Guide—Version 1.2," cantatabio.com, available on or before Aug. 8, 2022, retrieved from URL <https://dovetailgenomics.com/wp-content/uploads/securepdfs/2022/07/Dovetail%C2%AE-Micro-C-Kit-User-Guide-Version-1.2.pdf>, 29 pages.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Davis et al., "Glioblastoma: Overview of Disease and Treatment," Clin J Oncol Nurs, Oct. 2016, 20(5):S2-S8.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deininger et al., "Allograft inflammatory factor-1 defines a distinct subset of infiltrating macrophages/microglial cells in rat and human gliomas," Acta Neuropathol, Dec. 2000, 100(6):673-680.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.

(56) References Cited

OTHER PUBLICATIONS

Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eastburn, "Microfluidic droplet enrichment for targeted sequencing," Nucleic Acids Research, 2015, 43(13):1-8.
Eberwine, "Amplification of mRNA populations using aRNA generated from immobilized oligo(dT)-T7 primed cDNA," BioTechniques, 1996, 20(4):584-91.
Ecseq, "Trimming adapter sequences—is it necessary?" ecSEQ Bioinformatics, updated Aug. 7, 2016, retrieved from URL <https://www.ecseq.com/support/ngs/trimming-adapter-sequences-is-it-necessary>, 3 pages.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging in Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadrup et al., "Parallel detection of antigen-specific T-cell responses by multidimensional encoding of MHC multimers," Nat. Methods., Jul. 2009, 6(7), 520-526.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.

(56) References Cited

OTHER PUBLICATIONS

Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I—Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hobro et al, "An evaluation of fixation methods: Spatial and compositional cellular changes observed by Raman imaging," Vibrational Spectroscopy, Jul. 2017, 91:31-45.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jiang et al., "Skewer: a fast and accurate adapter trimmer for next-generation sequencing paired-end reads," BMC Bioinformatics, 2014, retrieved on Jun. 15, 2023, retrieved from URL <https://bmcbioinformatics.biomedcentral.com /articles/10.1186/1471-2105-15-182>, 15:182, pp. 1-12.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA-protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "A Ligase-Mediated Gene Detection Technique," Science, 1988, 241(4869):1077-1080.
Landegren et al., "Reading bits of genetic information: methods for single-nucleotide polymorphism analysis," Genome Res., Aug. 1998, 8(8):769-76.

(56) References Cited

OTHER PUBLICATIONS

Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Mamedov et al., "Preparing unbiased T-cell receptor and antibody cDNA libraries for the deep next generation sequencing profiling," Frontiers in Immunol., Dec. 23, 2013, 4(456):1-10.
Manz et al., "Phylogenetic Composition, Spatial Structure, and Dynamics of Lotic Bacterial Biofilms Investigated by Fluorescent in situ Hybridization and Confocal Laser Scanning Microscopy," Microb Ecol, May 1999, 37(4):225-237.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.

(56) References Cited

OTHER PUBLICATIONS

Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Oksuz et al., "Systematic evaluation of chromosome conformation capture assays," Nature Methods, Sep. 2021, 18:1046-1055.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
PCT International Search Report and Written Opinion in International Appln. No. PCT/US2022/042320, dated Dec. 19, 2022, 15 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gene," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rohland et al., "Partial uracil-DNA-glycosylase treatment for screening of ancient DNA," Phil. Trans. R. Soc. B, Jan. 19, 2015, 370(1660): 20130624, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.

(56) References Cited

OTHER PUBLICATIONS

Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schmidl et al., "ChIPmentation: fast, robust, low-input ChIP-seq for histones and transcription factors," Nature Methods, Oct. 2015, 12:963-965.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Sharma et al., "Melanopsichium pennsylvanicum 4 genomic scaffold, scaffold SCAFFOLD32," GenBank:HG529673.1, Ecology and Evolution, Biodiversity and Climate Research Center, Jan. 12, 2016, retrieved on Jun. 15, 2023, retrieved from URL <https://www.ncbi.nlm.nih.gov/nuccore/hg529673>.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Su et al., "Restriction enzyme selection dictates detection range sensitivity in chromatin conformation capture-based variant-to-gene mapping approaches," bioRxiv, Dec. 15, 2020, 22 pages.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.

(56) References Cited

OTHER PUBLICATIONS

Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 Rna ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Analysis of the expression profile of Dickkopf-1 gene in human glioma and the associate with tumor malignancy," Journal of Experimental & Clinical Cancer Research, Oct. 28, 2010, 29(138):1-7.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
10x Genomics, "Assay Scheme and Configuration of Chromium™ Single Cell V(D)J Libraries," 10x Genomics, CG000109 Rev D, 2017, 10 pages.
Deng et al., "Spatial-ATAC-seq: spatially resolved chromatin accessibility profiling of tissues at genome scale and cellular level," bioRxiv, Jun. 7, 2021, retrieved from URL <https://www.biorxiv.org/content/10.1101/2021.06.06.447244v1>, 49 pages (Preprint).
Hong et al., "Cell Microarray Technologies for High-Throughput Cell-Based Biosensors," Sensors (Basel), Jun. 5, 2017, 17(6):1293.
Stickels et al., "Highly sensitive spatial transcriptomics at near-cellular resolution with Slide-seqV2," Nat Biotechnol., Mar. 2021, 39(3):313-319, 28 pages (Author Manuscript).

METHODS, COMPOSITIONS, AND KITS FOR BLOCKING A CAPTURE PROBE ON A SPATIAL ARRAY

CROSS-REFERENCE TO RELATED APPLICATIONS

This application is a continuation application of U.S. patent application Ser. No. 18/226,933, now U.S. Pat. No. 11,840,724 filed on Jul. 27, 2023, which is a continuation application of U.S. application Ser. No. 18/181,263, now U.S. Pat. No. 11,753,673, filed on Mar. 9, 2023, which is a continuation of International Application PCT/US2022/042320, with an international filing date of Sep. 1, 2022, which claims the benefit of U.S. Provisional Patent Application No. 63/239,612, filed on Sep. 1, 2021, the content of which is incorporated herein by reference in its entirety.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Some techniques for studying spatial heterogeneity of a biological sample can cause analytes (e.g., nucleic acids) from the biological sample to diffuse to areas adjacent to the biological sample and be captured in such areas adjacent to the biological sample, or not as proximate to the original location of the analyte in the biological sample as is desired. The capturing of analytes on areas adjacent to the biological sample on the array (e.g., areas that are not covered by the biological sample) can lead to wasted resources, such as for example, unnecessary costs attributed to sequencing (e.g., next generation sequencing) as well as decreased resolution and accuracy of the spatial information from the biological sample. Thus, methods to decrease the incidence of captured analytes on areas of the array adjacent to the biological sample (e.g., by decreasing capture of analytes on areas not covered by the biological sample), can improve efficiency, resource conservation, and resolution of results.

SUMMARY

This application generally features methods to block capture probes on an array (e.g., a spatial array) that are not under or covered by a biological sample placed on the array. Methods described herein include methods to block capture probes on a spatial array using terminal deoxynucleotidyl transferase (TdT) and one or more dideoxynucleotides. The methods described herein can provide an improvement in resource conservation (e.g., reduced library for sequencing) and a reduction and/or elimination of binding (e.g., of analytes to unintended portions of the spatial array (e.g., portions of the array not under or covered by the biological sample) during performance of any of the methods described herein (e.g., determining a location of a target analyte in a biological sample).

Provided herein are methods for determining a location of a target nucleic acid in a biological sample, the method including: (a) disposing a biological sample onto an array at a first rea, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array; (b) contacting the second area of the array with a solution including terminal deoxynucleotidyl transferase and one or more dideoxynucleotides, such that one or more dideoxynucleotides are incorporated into the capture domain of the second capture probe; (c) removing residual solution from the second area of the array; (d) permeabilizing the biological sample, such that the capture domain of the first capture probe hybridizes to the target nucleic acid from the biological sample; and (e) determining (i) a sequence corresponding to the spatial barcode of the first capture probe, or a complement thereof, and (ii) all or a portion of a sequence corresponding to the target nucleic acid, or a complement thereof, and using the sequences of (i) and (ii) to determine the location of the target nucleic acid in the biological sample.

In some embodiments, the removing step includes the use of a wash buffer including one or more of: a solvent, an acid, a base, and a buffer. In some embodiments, the wash buffer includes phosphate buffered saline or saline sodium citrate.

In some embodiments, the determining in step (e) includes extending a 3' end of the capture probe of the first area of the array using the target nucleic acid as a template. In some embodiments, the determining in step (e) includes sequencing (i) the spatial barcode of the capture probe of the first area of the array, or a complement thereof, and (ii) all or a portion of the target nucleic acid, or a complement thereof. In some embodiments, the sequencing is high throughput sequencing.

In some embodiments, the permeabilizing includes use of a permeabilization agent selected from an organic solvent, a detergent, an enzyme, and combinations thereof. In some embodiments, the permeabilization agent is selected from the group consisting of: an endopeptidase, a protease, sodium dodecyl sulfate, polyethylene glycol tert-octylphenyl ether, polysorbate 80, polysorbate 20, N-lauroylsarcosine sodium salt solution, saponin, TRITON-X-100™ (t-octylphenoxypolyethoxyethanol), and TWEEN-20™ (polysorbate 20). In some embodiments, the endopeptidase is pepsin or proteinase K.

Also provided herein are methods of blocking capture probes not covered by a biological sample, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array; and (b) contacting the second area of the array with a solution including terminal deoxynucleotidyl transferase and one or more dideoxynucleotides, such that one or more dideoxynucleotides are incorporated into the capture domain of the second capture probe in the second area.

In some embodiments, the method includes step (c) permeabilizing the biological sample, such that the capture domain of the first capture probe hybridizes to the target nucleic acid from the biological sample. In some embodiments, step (c) includes contacting the biological sample with a permeabilization agent, where the permeabilization agent is selected from an organic solvent, a detergent, an enzyme, and combinations thereof. In some embodiments, the permeabilization agent is selected from the group consisting of: an endopeptidase, a protease, sodium dodecyl sulfate, polyethylene glycol tert-octylphenyl ether, polysorbate 80, polysorbate 20, N-lauroylsarcosine sodium salt solution, saponin, TRITON-X-100™ (t-octylphenoxypolyethoxyethanol), and TWEEN-20™ (polysorbate 20). In some embodiments, the endopeptidase is pepsin or proteinase K.

In some embodiments, the method includes removing residual solution from the second area of the array prior to permeabilization. In some embodiments, the removing step includes the use of a wash buffer including one or more of a solvent, an acid, a base, and a buffer. In some embodiments, the wash buffer includes phosphate buffered saline or saline sodium citrate.

In some embodiments, the biological sample is fixed and/or stained prior to step (a). In some embodiments, the method includes, between steps (a) and (b), fixing and/or staining the biological sample.

In some embodiments, the step of fixing the biological sample includes the use of a fixative selected from the group consisting of: ethanol, methanol, acetone, formaldehyde, paraformaldehyde-Triton, glutaraldehyde, and combinations thereof.

In some embodiments, the step of staining the biological sample includes the use of eosin and/or hematoxylin.

In some embodiments, the step of staining the biological sample includes the use of a detectable label selected from the group consisting of a radioisotope, a fluorophore, a chemiluminescent compound, a bioluminescent compound, and a combination thereof.

Also provided herein are methods for determining a location of a target nucleic acid in a biological sample, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array, where the capture domain of the first capture probe hybridizes to a ligation product; (b) extending the ligation product toward the 5' end of the first capture probe using the first capture probe as a template; (c) contacting the second area of the array with a solution including terminal deoxynucleotidyl transferase and one or more dideoxynucleotides, such that one or more dideoxynucleotides are incorporated into the capture domain of the second capture probe; (d) removing residual solution from the second area of the array; and (e) determining (i) a sequence corresponding to the spatial barcode of the first capture probe, or a complement thereof, and (ii) all or a portion of a sequence corresponding to the ligation product, or a complement thereof, and using the sequences of (i) and (ii) to determine the location of the target nucleic acid in the biological sample.

In some embodiments, the removing step includes the use of a wash buffer including one or more of: a solvent, an acid, a base, and a buffer. In some embodiments, the wash buffer includes phosphate buffered saline or saline sodium citrate.

In some embodiments, the extending in step (b) includes extending a 3' end of the first capture probe using the ligation product as a template.

In some embodiments, the determining in step (e) includes sequencing (i) the spatial barcode of the first capture probe, or a complement thereof, and (ii) all or a portion of the ligation product, or a complement thereof. In some embodiments, the sequencing is high throughput sequencing.

Also provided herein are methods of blocking capture probes to decrease barcode exchange and/or decrease the use of capture probes as extension templates, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array, where the capture domain of the first capture probe hybridizes to a ligation product; (b) extending the ligation product toward the 5' end of the first capture probe using the first capture probe as a template; and (c) contacting the second area of the array with a solution including terminal deoxynucleotidyl transferase and one or more dideoxynucleotides, such that one or more dideoxynucleotides are incorporated into the capture domain of the second capture probe.

In some embodiments, the method includes removing residual solution from the second area of the array. In some embodiments, the removing step includes the use of a wash buffer including one or more of a solvent, an acid, a base, and a buffer. In some embodiments, the wash buffer includes phosphate buffered saline or saline sodium citrate.

In some embodiments, the biological sample is fixed and/or stained prior to step (a). In some embodiments, the method includes, between steps (a) and (b), fixing and/or staining the biological sample.

In some embodiments, the step of fixing the biological sample includes the use of a fixative selected from the group consisting of ethanol, methanol, acetone, formaldehyde, paraformaldehyde-Triton, glutaraldehyde, and combinations thereof. In some embodiments, the step of staining the biological sample includes the use of eosin and/or hematoxylin.

In some embodiments, the step of staining the biological sample includes the use of a detectable label selected from the group consisting of a radioisotope, a fluorophore, a chemiluminescent compound, a bioluminescent compound, and a combination thereof.

In some embodiments, the ligation product is generated by hybridizing a first probe and a second probe to the target nucleic acid, where the first probe and the second probe are ligated to form the ligation product. In some embodiments, the first probe or the second probe includes an analyte capture sequence that hybridizes to the capture domain of the first capture probe.

In some embodiments, the one or more dideoxynucleotides is ddATP or ddTTP. In some embodiments, the solution includes about 0.5 mM of the one or more dideoxynucleotides to about 25 mM of the one or more dideoxynucleotides. In some embodiments, the solution includes about 0.5 mM of the one or more dideoxynucleotides to about 1.5 mM of the one or more dideoxynucleotides. In some embodiments, the solution includes about 1 mM of the one or more dideoxynucleotides.

In some embodiments, the solution includes $CoCl_2$. In some embodiments, the solution includes about 0.1 mM $CoCl_2$ to about 2 mM $CoCl_2$. In some embodiments, the solution includes about 0.25 mM $CoCl_2$.

In some embodiments, the solution includes a buffer.

In some embodiments, the contacting step is performed for about 5 minutes to about 90 minutes. In some embodiments, the contacting step is performed for about 60 minutes. In some embodiments, the contacting step is performed at a temperature of about 25° C. to about 45° C. In some embodiments, the contacting step is performed at a temperature of about 37° C.

Also provided herein are kits including: (a) a solution including terminal deoxynucleotidyl transferase; (b) one or more dideoxynucleotides; (c) a substrate including a plurality of capture probes, where a capture probe of the plurality of capture probes include a spatial barcode and a capture domain; and (d) instructions for performing any of the methods described herein.

In some embodiments, the kit includes a fixative selected from the group consisting of ethanol, methanol, acetone, formaldehyde, paraformaldehyde-Triton, glutaraldehyde, and combinations thereof.

In some embodiments, the one or more dideoxynucleotides are ddATP and/or ddTTP. In some embodiments, the solution includes about 0.5 mM of the one or more dideoxynucleotides to about 25 mM of the one or more dideoxynucleotides. In some embodiments, the solution includes about 0.5 mM of the one or more dideoxynucleotides to about 1.5 mM of the one or more dideoxynucleotides. In some embodiments, the solution includes about 1 mM of the one or more dideoxynucleotides.

In some embodiments, the solution includes $CoCl_2$. In some embodiments, the solution includes about 0.1 mM $CoCl_2$ to about 2 mM $CoCl_2$. In some embodiments, the solution includes about 0.25 mM $CoCl_2$.

In some embodiments, the solution includes a buffer. In some embodiments, the kit includes a wash buffer including one or more of: a solvent, an acid, a base, and a buffer. In some embodiments, the wash buffer includes phosphate buffered saline. In some embodiments, the wash buffer includes saline sodium citrate.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
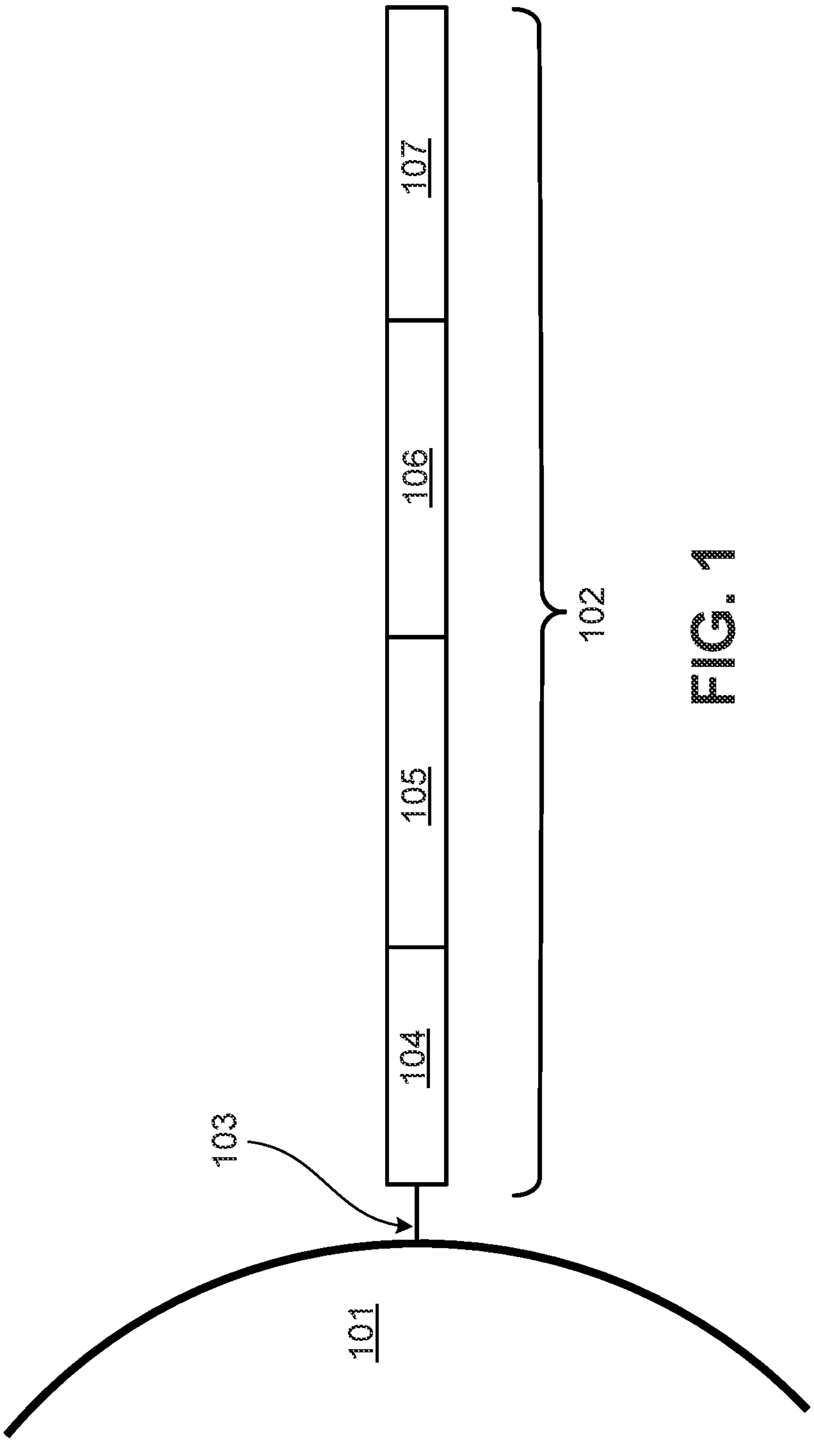
FIG. 1 is a schematic diagram showing an example of a barcoded capture probe, as described herein.

The result of capturing nucleic acid analytes, or proxies thereof, on areas adjacent to a biological sample on an array (e.g., areas that are not under or covered with the biological sample) can lead to wasted resources, such as unnecessary costs attributed to sequencing (e.g., next generation sequencing) and can compromise spatial resolution. Blocking one or more capture domains of capture probes on spatial arrays (or portions thereof) can increase efficiency and/or decrease binding of analytes on arrays (or portions thereof). In some cases, one or more capture probes (e.g., capture domain of capture probes) can be blocked using terminal deoxynucleotidyl transferase and one or more dideoxynucleotides. Provided herein are methods, compositions, and kits for carrying out these methods.

Methods for reducing spatial interactions on a spatial array on areas not under or covered by a biological sample are described herein. The methods described herein can improve the resolution of spatial array results by reducing binding of nucleic acid analytes or proxies thereof on areas of the array that do not correlate with the original location of the biological sample on the array. In some cases, nucleic acid analytes from a biological sample can diffuse (e.g., laterally) to areas of the array that are not covered by the biological sample, which can result in analytes binding to the capture domain(s) of one or more capture probes not covered by the biological sample. Analyte capture on areas adjacent or proximal to the biological sample increase background results and decrease resolution. Blocking the capture domain of capture probes that are adjacent or proximal to the biological sample can decrease the unwanted binding and increase the resolution of target capture. Thus, the present disclosure features methods, compositions, and kits that can reduce the capture of nucleic acid analytes on areas adjacent to or not covered by the biological sample by preventing binding of analytes to those capture probes adjacent or proximal to the biological sample (e.g., by blocking the capture domain of capture probes).

The methods described herein can also conserve resources. For example, in some cases, the analysis of data obtained from nucleic analytes captured on an array (e.g., a spatial array) can include sequencing. Unwanted binding of nucleic acid analytes to the capture domain of one or more capture probes can result in sequencing of nucleic acid analytes captured in areas not covered by the biological sample. Unwanted nucleic acid analyte capture (or proxies thereof) can also cause downstream sequencing inefficiencies, for example, a decrease in the amount of nucleic acid analyte sequencing due to sequencing of unwanted captured analytes is inefficient and reagent costly and can result in a decrease in spatial resolution. The present disclosure provides solutions for improving and/or preventing unwanted nucleic acid analyte (or proxies thereof capture on an array.

The methods described herein include blocking the capture domain of one or more capture probes located in areas not under or covered by a biological sample on an array using terminal deoxynucleotidyl transferase and nucleotide triphosphates. Terminal deoxynucleotidyl transferase can transfer nucleotide triphosphates to the 3' hydroxyl end of oligonucleotides. For example, incorporating one or more dideoxynucleotides into the 3' end of a capture probe with terminal deoxynucleotidyl transferase can prevent ligation or polymerase extensions, including reverse transcription.

In some embodiments, terminal deoxynucleotidyl transferase and one or more dideoxynucleotides are applied to the portions of the array that are not covered by a biological sample prior to permeabilization of the biological sample. In this way, the extension of capture probes that are not under or covered by the biological sample is prevented. This can reduce wasted resources by prevention of reads from capture probes in areas adjacent to the biological sample, and also reduce mislocalized analytes that may appear in voids or spaces in the biological sample (e.g., airways in biological samples such as lung tissue). In other embodiments, applying terminal deoxynucleotidyl transferase and one or more dideoxynucleotides after second strand synthesis, but prior to amplification, can reduce or eliminate barcode exchange that results from capture probes acting as extension templates (e.g., primers).

As used herein "barcode exchange" or a "barcode exchange reaction" refers to excess or extra barcoded molecules (e.g., capture probes that include a spatial barcode) that function as extension templates. As used herein capture probes not covered by the biological sample can function as an extension template and introduce a different barcode (e.g., a spatial barcode) than the parent template molecule during amplification such as second strand synthesis. In some examples, barcode exchange can occur during preparation of sequencing libraries. Barcode exchange and barcode exchange reactions are further described in WO 2020/028882, which is incorporated herein by reference in its entirety.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides incorporated (e.g., added) to the terminus (e.g., 3' or 5' end) of the capture probe thereby extending the overall length of the capture probe. For example, an "extended 3' end" indicates additional incorporated nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A “feature” is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, “contact,” “contacted,” and/or “contacting,” a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., Splint® ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Methods for Reducing Unwanted Target Nucleic Acid Capture or Proxies Thereof on an Array Spatial arrays provide researchers the tools to identify gene expression, protein locations, and/or other cellular activity in a spatial manner. The benefits of correlating spatial biological relationships with diseases and disorders does, and will, continue to advance many fields of scientific study. However, improvements in the resolution of spatial relationships between cellular activities and diseases and disorders would enhance those data. For example, when a biological sample (e.g., a tissue section) placed on a spatial array is permeabilized to release target nucleic acids, some of the nucleic acids from the biological sample can, via diffusion, move to areas of the array where there is no biological sample (e.g., tissue section), for example adjacent to or not covered by the biological sample, where unwanted nucleic acid analyte capture can occur. This type of unwanted nucleic acid or proxy thereof capture can decrease the resolution of the desired spatial data. Further, unwanted nucleic acid capture can cause downstream sequencing inefficiencies; a decrease in the amount of target nucleic acid sequencing due to sequencing of unwanted captured nucleic acids or proxies thereof is inefficient and reagent costly. The present disclosure provides solutions for improving and/or preventing unwanted nucleic acid capture on an array on areas adjacent to and/or not covered by the biological sample.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

The methods herein describe blocking a capture domain of one or more capture probes using terminal deoxynucleotidyl transferase (TdT) and one or more dideoxynucleotides. TdT can transfer one or more dideoxynucleotides to the 3' hydroxyl end of the capture domain of a capture probe which prevents ligation or polymerase extension reactions (e.g., reverse transcription reactions).

In some embodiments, the methods herein describe blocking a capture domain of one or more capture probes by applying TdT and one or more dideoxynucleotides to the array prior to permeabilization of the biological sample. This can prevent extending the capture domain by reverse transcription of one or more capture probes that are not covered by the biological sample (e.g., in areas not covered by the biological sample). Blocking the capture domain can conserve resources, reduce wasted sequencing reads, and reduce mislocalized transcripts that appear in voids or spaces or tears of tissue (e.g., airways that may be found in lung tissue sections).

Provided herein are methods for determining a location of a target nucleic acid in a biological sample, the method including: (a) disposing a biological sample onto an array at a first rea, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array; (b) contacting the second area of the array with a solution including terminal deoxynucleotidyl transferase and one or more dideoxynucleotides, such that one or more dideoxynucleotides are incorporated into the capture domain of the second capture probe; (c) removing residual solution from the second area of the array; (d) permeabilizing the biological sample, such that the capture domain of the first capture probe hybridizes to the target nucleic acid from the biological sample; and (e) determining (i) a sequence corresponding to the spatial barcode of the first capture probe, or a complement thereof, and (ii) all or a portion of a sequence corresponding to the target nucleic acid, or a complement thereof, and using the sequences of (i) and (ii) to determine the location of the target nucleic acid in the biological sample.

Also provided herein are methods of blocking capture probes not covered by a biological sample, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array; and (b) contacting the second area of the array with a solution including terminal deoxynucleotidyl transferase and one or more dideoxynucleotides, such that one or more dideoxynucleotides are incorporated into the capture domain of the second capture probe in the second area.

In some embodiments, a solution including terminal deoxynucleotidyl transferase and one or more dideoxynucleotides is applied to the array to prevent barcode exchange that can result from capture probes acting as extension templates. For example, the solution including terminal deoxynucleotidyl transferase and one or more dideoxynucleotides can be applied to the array after extending a 3' end of the first capture probe and/or after generating a second strand of nucleic acid complementary to the cDNA.

In some embodiments, a solution including terminal deoxynucleotidyl transferase and one or more dideoxynucleotides is applied to a biological sample on an array and removed prior to tissue permeabilization.

Also provided herein are methods for determining a location of a target nucleic acid in a biological sample, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array, where the capture domain of the first capture probe hybridizes to a ligation product; (b) extending the ligation product toward the 5' end of the first capture probe using the first capture probe as a template; (c) contacting the second area of the array with a solution including terminal deoxynucleotidyl transferase and one or more dideoxynucleotides, such that one or more dideoxynucleotides are incorporated into the capture domain of the second capture probe; (d) removing residual solution from the second area of the array; and (e) determining (i) a sequence corresponding to the spatial barcode of the first capture probe, or a complement thereof, and (ii) all or a portion of a sequence corresponding to the ligation product, or a complement thereof, and using the sequences of (i) and (ii) to determine the location of the target nucleic acid in the biological sample.

Also provided herein are methods of blocking capture probes to decrease barcode exchange and/or decrease the use of capture probes as extension templates, the method including: (a) disposing a biological sample onto an array at a first area, where the array includes a plurality of capture probes, where: a first capture probe of the plurality of capture probes includes a spatial barcode and a capture domain, where the first capture probe is included in the first area of the array; and a second area of the array includes a second capture probe of the plurality of capture probes including a spatial barcode and a capture domain, where the second area is not covered by the biological sample disposed on the array, where the capture domain of the first capture probe hybridizes to a ligation product; (b) extending the ligation product toward the 5' end of the first capture probe using the first capture probe as a template; and (c) contacting the second area of the array with a solution including terminal deoxynucleotidyl transferase and one or more dideoxynucleotides, such that one or more dideoxynucleotides are incorporated into the capture domain of the second capture probe.

The biological sample can be any of the biological samples described herein. For example, in some embodiments, the biological sample is a tissue sample. In some embodiments, the tissue sample is a fresh-frozen tissue sample. In some embodiments, the tissue sample is a fixed tissue sample (e.g., fixed by any of the fixatives described herein). In some embodiments, the biological sample is a tissue section. In some embodiments, the tissue section is a fresh-frozen tissue section. In some embodiments, the tissue section is a fixed tissue section (e.g., fixed by any of the fixatives described herein). In other embodiments, the biological sample is a clinical sample (e.g., whole blood, blood cells, cultured tissue, cultured cells, or a cell suspension). In some embodiments, the biological sample is an organoid, embryonic stem cells, pluripotent stem cells, or any combination thereof. Non-limiting examples of an organoid include a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, a retinal organoid, or any combination thereof. In other example embodiments, the biological sample can include diseased cells, fetal cells, immune cells, cellular macromolecules, organelles, extracellular polynucleotides, or any combination thereof.

Non-limiting examples of a target nucleic acid include DNA analytes such as genomic DNA, methylated DNA, specific methylated DNA sequences, fragmented DNA, mitochondrial DNA, in situ synthesized PCR products, and viral DNA.

Non-limiting examples of a target nucleic acid also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA). The RNA can be from an RNA virus, for example RNA viruses from Group III, IV or V of the Baltimore classification system. The RNA can be from a retrovirus, such as a virus from Group VI of the Baltimore classification system.

In some embodiments, the target nucleic acid can include at least 1, at least 2, at least 3, at least 4, at least 5, at least 6, at least 7, at least 8, at least 9, or at least 10 disease-causing mutations (e.g., cancer-causing mutations). In some embodiments, the target nucleic acid includes a single nucleotide polymorphism, gene amplification, or chromosomal translocation, deletion or insertion.

In some embodiments, the method includes removing the residual solution (e.g., washing the array using any of the methods for removing solutions described herein) from the biological sample prior to permeabilization. In some embodiments, the biological sample can be fixed (e.g., the biological sample can be fixed using any of the techniques described herein or known in the art). In some embodiments, fixing the biological sample includes the use of a fixative such as ethanol, methanol, acetone, formaldehyde, formalin, paraformaldehyde-Triton, glutaraldehyde, or any combination thereof. In some embodiments, a fixed biological sample is a formalin-fixed paraffin-embedded tissue sample. In some embodiments, a fixed biological sample is a formalin-fixed paraffin-embedded tissue section. In some embodiments, the biological sample can be fixed (e.g., after step (a), or between steps (a) and (b), the biological sample can be fixed using any of the techniques described herein or known in the art).

In some embodiments, the biological sample can be stained and/or imaged using any of the techniques described herein or known in the art (e.g., the biological sample can be stained and/or imaged after step (a), or between steps (a) and (b)). In some embodiments, staining includes optical labels as described herein, including, but not limited to, fluorescent (e.g., fluorophore), radioactive (e.g., radioisotope), chemiluminescent (e.g., a chemiluminescent compound), a bioluminescent compound, calorimetric, or colorimetric detectable labels. In some embodiments, staining includes a fluorescent antibody directed to a target analyte (e.g., cell surface or intracellular proteins) in the biological sample. In some embodiments, staining includes an immunohistochemistry stain directed to a target analyte (e.g., cell surface or intracellular proteins) in the biological sample. In some embodiments, staining includes a chemical stain, such as hematoxylin and eosin (H&E) or periodic acid-schiff (PAS). In some embodiments, staining the biological sample includes the use of a biological stain including, but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof. In some embodiments, significant time (e.g., days, months, or years) can elapse between staining and/or imaging the biological sample.

In some embodiments, the determining includes extending a 3' end of the capture probe of the first area of the array using the target nucleic acid as a template. In some embodiments, the determining includes sequencing (i) the spatial barcode of the first capture probe of the array, or a complement thereof, and (ii) all or a portion of the target nucleic acid, or a complement thereof. In some embodiments, the determining includes sequencing (i) the spatial barcode of the first capture probe of the array, or a complement thereof, and (ii) all or a portion of a ligation product, or a complement thereof.

In some embodiments, permeabilizing the biological sample includes contacting the biological sample with a permeabilization agent. In some embodiments, the permeabilization agent includes the use of an organic solvent, a detergent, an enzyme, or combinations thereof. The permeabilization agent can include: an endopeptidase, a protease, sodium dodecyl sulfate (SDS), polyethylene glycol tert-octylphenyl ether, polysorbate 80, and polysorbate 20, N-lauroylsarcosine sodium salt solution, saponin, TRITON-X-100™ (t-octylphenoxypolyethoxyethanol), and TWEEN-20™ (polysorbate 20). In some embodiments, the endopeptidase is pepsin or proteinase K.

In some embodiments, the biological sample is imaged prior to permeabilization.

First and Second Areas

In some embodiments of any of the methods described herein, an array can have a first area upon which a biological sample is disposed and a second area that is adjacent to (e.g., not covered by) the biological sample. For instance, some embodiments of any of the methods described herein include disposing a biological sample onto an array (e.g., any of the exemplary arrays described herein), where the array has a first area covered by the biological sample and a second area not covered by the biological sample.

In some examples, the first area can represent a portion of the array that is covered by the biological sample, e.g., about 10% to about 99%, about 10% to about 95%, about 10% to about 90%, about 10% to about 85%, about 10% to about 80%, about 10% to about 75%, about 10% to about 70%, about a 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about a 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 99%, about 20% to about 95%, about 20% to about 90%, about 20% to about 85%, about 20% to about 80%, about 20% to about 75%, about 20% to about 70%, about a 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 99%, about 25% to about 95%, about 25% to about 90%, about 25% to about 85%, about 25% to about 80%, about 25% to about 75%, about 25% to about 70%, about a 25% to about 65%, about 25% to about 60%, about 25% to about 55%, about 25% to about 50%, about 25% to about 45%, about 25% to about 40%, about 25% to about 35%, about 25% to about 30%, about 30% to about 99%, about 30% to about 95%, about 30% to about 90%, about 30% to about 85%, about 30% to about 80%, about 30% to about 75%, about 30% to about 70%, about a 30% to about 65%, about 30% to about 60%, about 30% to about 55%, about 30% to about 50%, about 30% to about 45%, about 30% to about 40%, about 30% to about 35%, about 35% to about 99%, about 35% to about 95%, about 35% to about 90%, about 35% to about 85%, about 35% to about 80%, about 35% to about 75%, about 35% to about 70%, about a 35% to about 65%, about 35% to about 60%, about 35% to about 55%, about 35% to about 50%, about 35% to about 45%, about 35% to about 40%, about 40% to about 99%, about 40% to about 95%, about 40% to about 90%, about 40% to about 85%, about 40% to about 80%, about 40% to about 75%, about 40% to about 70%, about a 40% to about 65%, about 40% to about 60%, about 40% to about 55%, about 40% to about 50%, about 40% to about 45%, about 45% to about 99%, about 45% to about 95%, about 45% to about 90%, about 45% to about 85%, about 45% to about 80%, about 45% to about 75%, about 45% to about 70%, about a 45% to about 65%, about 45% to about 60%, about 45% to about 55%, about 45% to about 50%, about 50% to about 99%, about 50% to about 95%, about 50% to about 90%, about 50% to about 85%, about 50% to about 80%, about 50% to about 75%, about 50% to about 70%, about a 50% to about 65%, about 50% to about 60%, about 50% to about 55%, about 55% to about 99%, about 55% to about 95%, about 55% to about 90%, about 55% to about 85%, about 55% to about 80%, about 55% to about 75%, about 55% to about 70%, about a 55% to about 65%, about 55% to about 60%, about 60% to about 99%, about 60% to about 95%, about 60% to about 90%, about 60% to about 85%, about 60% to about 80%, about 60% to about 75%, about 60% to about 70%, about a 60% to about 65%, about 65% to about 99%, about 65% to about 95%, about 65% to about 90%, about 65% to about 85%, about 65% to about 80%, about 65% to about 75%, about 65% to about 70%, about 70% to about 99%, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99%, of the total area of the array covered by the biological sample.

The second area represents a portion of the array that is not covered by the biological sample.

Solution of Terminal Deoxynucleotidyl Transferase and One or More Dideoxynucleotides The solution of terminal deoxynucleotidyl transferase and one or more dideoxynucleotides can include a buffer. In some embodiments, the solution includes about 0.5 mM of the dideoxynucleotides to about 25 mM of the dideoxynucleotides (e.g., about 0.5 mM to about 24.5 mM, about 0.5 mM to about 24 mM, about 0.5 mM to about 23.5 mM, about 0.5 mM to about 23 mM, about 0.5 mM to about 22.5 mM, about 0.5 mM to about 22 mM, about 0.5 mM to about 21.5 mM, about 0.5 mM to about 21 mM, about 0.5 mM to about 20.5 mM, about 0.5 mM to about 20 mM, about 0.5 mM to about 19.5 mM, about 0.5 mM to about 19 mM, about 0.5 mM to about 18.5 mM, about 0.5 mM to about 18 mM, about 0.5 mM to about 17.5 mM, about 0.5 mM to about 17 mM, about 0.5 mM to about 16.5 mM, about 0.5 mM to about 16 mM, about 0.5 mM to about 15.5 mM, about 0.5 mM to about 15 mM, about 0.5 mM to about 14.5 mM, about 0.5 mM to about 14 mM, about 0.5 mM to about 13.5 mM, about 0.5 mM to about 13 mM, about 0.5 mM to about 12.5 mM, about 0.5 mM to about 12 mM, about 0.5 mM to about 11.5 mM, about 0.5 mM to about 11 mM, about 0.5 mM to about 10.5 mM, about 0.5 mM to about 10 mM, about 0.5 mM to about 9.5 mM, about 0.5 mM to about 9 mM, about 0.5 mM to about 8.5 mM, about 0.5 mM to about 8 mM, about 0.5 mM to about 7.5 mM, about 0.5 mM to about 7 mM, about 0.5 mM to about 6.5 mM, about 0.5 mM to about 6 mM, about 0.5 mM to about 5.5 mM, about 0.5 mM to about 5 mM, about 0.5 mM to about 4.5 mM, about 0.5 mM to about 4 mM, about 0.5 mM to about 3.5 mM, about 0.5 mM to about 3 mM, about 0.5 mM to about 2.5 mM, about 0.5 mM to about 2 mM, about 0.5 mM to about 1.5 mM, or about 0.5 mM to about 1 mM). In some embodiments, the buffer is a reaction buffer. In some embodiments, the solution includes about 0.02 mM to about 2.0 mM of the dideoxynucleotides. In some embodiments, the solution includes about 1 mM of the dideoxynucleotides. In some embodiments, the dideoxynucleotide is ddATP and/or ddTTP. In some embodiments, the dideoxynucleotide is ddCTP and/or ddGTP. In some embodiments, the dideoxynucleotides include a mixture of ddATP, ddTTP, ddCTP, and ddGTP.

In some embodiments, the solution of terminal deoxynucleotidyl transferase and one or more dideoxynucleotides can include $CoCl_2$. In some embodiments, the solution includes about 0.1 mM $CoCl_2$ to about 2 mM $CoCl_2$, (e.g., about 0.1 mM to about 1.8 mM, about 0.1 mM to about 1.6 mM, about 0.1 mM to about 1.4 mM, about 0.1 mM to about 1.2 mM, about 0.1 mM to about 1.0 mM, about 0.1 mM to about 0.8 mM, about 0.1 mM to about 0.6 mM, about 0.1 mM to about 0.4 mM, or about 0.1 mM to about 0.2 mM). In some embodiments, the solution includes about 0.25 mM $CoCl_2$. Other divalent cationic cofactors such as $Mg^{+2}$, $Mn^{+2}$, and $Zn^{+2}$ (e.g., salts of the divalent cations) can also be utilized by the TdT enzyme. A skilled artisan will understand that the rate of the enzymatic activity of TdT can depend upon one or both of the nucleotide and/or the cofactor being used in the reaction.

Contacting the Second Area of the Array with a Solution Including Terminal Deoxynucleotidyl Transferase and One or More Dideoxynucleotides In some embodiments, the solution including terminal deoxynucleotidyl transferase and one or more dideoxynucleotides is added automatically (e.g., by a device e.g., a robot) or manually (e.g., by pipetting) to the second area of the array. In some embodiments, the solution including terminal deoxynucleotidyl transferase and one or more dideoxynucleotides is added dropwise by a pipette. In some embodiments, the solution including terminal deoxynucleotidyl transferase and one or more dideoxynucleotides is added to contact all or a portion of the second area of the array. In some embodiments, the solution including terminal deoxynucleotidyl transferase and one or more dideoxynucleotides is added to all or a portion of a surface of the biological sample that is not facing or contacting the array. In some embodiments, the solution including terminal deoxynucleotidyl transferase and one or more dideoxynucleotides is added to the whole array.

In some embodiments, the solution is added vertically above the second area of the array. In some embodiments, the solution is present in liquid form, such that the second area is covered by the solution.

In some embodiments, the second area of the array can be contacted by the solution for, e.g., about 5 minutes to about 90 minutes, about 5 minutes to about 80 minutes, about 5 minutes to about 70 minutes, about 5 minutes to about 60 minutes, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour. In some embodiments, the contacting step is performed for about 60 minutes.

In some embodiments, the contacting step is performed at a temperature of about 4° C. to about 45° C., about 4° C. to about 40° C., about 4° C. to about 35° C., about 4° C. to about 30° C., about 4° C. to about 25° C., about 4° C. to about 20° C., about 4° C. to about 15° C., about 4° C. to about 10° C., about 10° C. to about 45° C., about 10° C. to about 40° C., about 10° C. to about 35° C., about 10° C. to about 30° C., about 10° C. to about 25° C., about 10° C. to about 20° C., about 10° C. to about 15° C., about 15° C. to about 45° C., about 15° C. to about 40° C., about 15° C. to about 35° C., about 15° C. to about 30° C., about 15° C. to about 25° C., about 15° C. to about 20° C., about 20° C. to about 45° C., about 20° C. to about 40° C., about 20° C. to about 35° C., about 20° C. to about 30° C., about 20° C. to about 25° C., about 25° C. to about 45° C., about 25° C. to about 40° C., about 25° C. to about 35° C., about 25° C. to about 30° C., or about 30° C. to about 45° C. In some embodiments, the contacting step is performed at a temperature of about 25° C. to about 45° C. In some embodiments, the contacting step is performed at a temperature of about 37° C.

Removing the Solution Including Terminal Deoxynucleotidyl Transferase and One or More Dideoxynucleotides from the Second Area of the Array In some embodiments, the solution including terminal deoxynucleotidyl transferase and one or more dideoxynucleotides is removed by pipetting. In some embodiments, the solution including terminal deoxynucleotidyl transferase and one or more dideoxynucleotides is removed by wicking (e.g., by an absorption paper). In some embodiments, the solution including terminal deoxynucleotidyl transferase and one or more dideoxynucleotides is removed by washing (e.g., using a wash buffer). In some embodiments, a wash buffer can be added to contact the first and/or second area of the array then removed by pipetting, wicking, or other methods known in the art. In some embodiments, a combination of removing methods can be used. In some embodiments, contacting and removing steps can be repeated (e.g., at least 2 times, 3 times, 4 times, or more). In some embodiments, a drying step can be performed after washing (e.g., air drying).

In some embodiments, the wash buffer is added automatically (e.g., by a robot) or manually (e.g., by pipetting). In some embodiments, the wash buffer is added vertically above the array. In some embodiments, the wash buffer is added vertically above the second area of the array. In some embodiments, the wash buffer is added dropwise by a pipette. In some embodiments, the wash buffer is added to contact all or a portion of the second area of the array. In some embodiments, the wash buffer is added to all or a portion of a surface of the biological sample that is not facing or contacting the array. In some embodiments, a wash buffer is added to the whole array including the first and second areas. In some embodiments, the washing buffer is 1×TE buffer, 1×TAE buffer, 1×TBE buffer, sodium saline citrate, or PBS. In some embodiments, the wash buffer contains a buffer (e.g., Tris, MOPS, HEPES, MES, or any other buffer known in the art), chelating agents (e.g., ethylenediaminetetraacetic acid (EDTA)), and/or metal ions (e.g., $Mg^{2+}$). In some embodiments, the wash buffer can have a pH that is about 5.0, about 5.5, about 6.0, about 6.5, about 7.0, about 7.5, about 8.0, about 8.5, about 9.0, about 9.5, or about 10.0, or about 5.0 to 5.5, about 5.5 to 6.0, about 6.0 to 6.5, about 6.5 to 7.0, about 7.0 to 7.5, about 7.5 to 8.0, about 8.0 to 8.5, about 8.5 to 9.0, about 9.0 to 9.5, or about 9.5 to 10.0.

In some embodiments, the second area of the array is contacted by the wash buffer for about 5 seconds to about 1 hour, about 5 seconds to about 50 minutes, about 5 seconds to about 40 minutes, about 5 seconds to about 30 minutes, about 5 seconds to about 20 minutes, about 5 seconds to about 10 minutes, about 5 seconds to about 5 minutes, about 5 seconds to about 1 minute, about 5 seconds to about 30 seconds, about 5 seconds to about 10 seconds, about 10 seconds to about 1 hour, about 10 seconds to about 50 minutes, about 10 seconds to about 40 minutes, about 10 seconds to about 30 minutes, about 10 seconds to about 20 minutes, about 10 seconds to about 10 minutes, about 10 seconds to about 5 minutes, about 10 seconds to about 1 minute, about 10 seconds to about 30 seconds, about 30 seconds to about 1 hour, about 30 seconds to about 50 minutes, about 30 seconds to about 40 minutes, about 30 seconds to about 30 minutes, about 30 seconds to about 20 minutes, about 30 seconds to about 10 minutes, about 30 seconds to about 5 minutes, about 30 seconds to about 1 minute, about 1 minute to about 1 hour, about 1 minute to about 50 minutes, about 1 minute to about 40 minutes, about 1 minute to about 30 minutes, about 1 minute to about 20 minutes, about 1 minute to about 10 minutes, about 1 minute to about 5 minutes, about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at a temperature of about 4° C. to about 35° C., about 4° C. to about 30° C., about 4° C. to about 25° C., about 4° C. to about 20° C., about 4° C. to about 15° C., about 4° C. to about 10° C., about 10° C. to about 35° C. to about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° to about 25° C., about 25° C. to about 35° C., about 25° C. to about 30° C., or about 30° C. to about 35° C.

Kits

Also provided herein are kits that include a solution including terminal deoxynucleotidyl transferase; one or more dideoxynucleotides, a substrate (e.g., an array) including a plurality of capture probes, where the capture probes include a spatial barcode and a capture domain; and instructions for performing any of the methods described herein.

In some embodiments, the kit can include one or more fixative(s) (e.g., any of the fixatives described herein) to fix the biological sample and/or preserve the structure of the biological sample. Non-limiting examples of a fixative include ethanol, methanol, acetone, formaldehyde (e.g., 2% formaldehyde), formalin, paraformaldehyde-Triton, glutaraldehyde, or any combination thereof.

In some embodiments, the kit includes about 0.5 mM of the dideoxynucleotides to about 25 mM of the dideoxynucleotides. In some embodiments, the dideoxynucleotide is ddATP. In some embodiments, the dideoxynucleotide is ddTTP. In some embodiments, the dideoxynucleotide is ddGTP. In some embodiments, the dideoxynucleotide is ddCTP. In some embodiments, the dideoxynucleotide is a mixture of ddATP, ddTTP, ddCTP, and ddGTP. In some embodiments, the solution includes about 0.5 mM of the dideoxynucleotide to about 1.5 mM of the dideoxynucleotide. In some embodiments, the solution includes about 1 mM of the dideoxynucleotide.

In some embodiments, the solution includes $CoCl_2$. In some embodiments, the solution includes about 0.1 mM $CoCl_2$ to about 2 mM $CoCl_2$. In some embodiments, the solution includes about 0.25 mM $CoCl_2$. In some embodiments, the solution includes about 0.1 mM to about 2 mM $MgCl_2$.

In some embodiments, the solution includes a buffer. In some embodiments, the kit includes a wash buffer including one or more of: a solvent, an acid, a base, and a buffer. In some embodiments, the wash buffer is phosphate buffered saline.

Compositions

The present disclosure also features compositions for blocking capture probes in an area (e.g., a second area) of an array not covered by a biological sample. Thus, provided herein are compositions including a biological sample disposed on an array at a first area, where the array includes a plurality of capture probes, wherein a first capture probe of the plurality of capture probes includes a spatial barcode and a capture domain, where the first capture probe is comprised in the first area of the array; where a second area of the array includes a second capture probe of the plurality of capture probes including a spatial barcode and a capture domain, where the second area is not covered by the biological sample disposed on the array; and a solution including terminal deoxynucleotidyl transferase and one or more dideoxynucleotides disposed on the second area of the array.

Also provided herein are compositions including a biological sample disposed on an array at a first area, where the first area includes a plurality of capture probes, where a first capture probe of the plurality of capture probes includes a spatial barcode and a capture domain, where the first capture probe is comprised in the first area of the array; a solution including terminal deoxynucleotidyl transferase and one or more dideoxynucleotides on a second area of the array; the second area of the array including a second capture probe of the plurality of capture probes including a spatial barcode and a capture domain, where the second area is not covered by the biological sample disposed on the array and the second capture probe in the second area is extended with one or more dideoxynucleotides.

Also provided herein are compositions including a an array including a first area and a second area, where the array includes a plurality of capture probes distributed across the first and second areas, where the first area includes a first capture probe of the plurality of capture probes including a spatial barcode and a capture domain; a solution including terminal deoxynucleotidyl transferase and one or more dideoxynucleotides disposed on the second area of the array; where the second area of the array includes a second capture probe of the plurality of capture probes including a spatial barcode and a capture domain, where the second capture probe is extended with one or more dideoxynucleotides. In some embodiments of this composition, the first capture probe is hybridized to a target nucleic acid from a biological sample or a proxy thereof (e.g., a ligation product). In some embodiments of this composition, the first capture probe is extended (e.g., by ligation or reverse transcription) to further include the reverse complement of a target nucleic acid from a biological sample or a proxy thereof (e.g., a ligation product).

In some embodiments, the composition includes a wash buffer. In some embodiments, the wash buffer includes one or more of a solvent, an acid, a base, and a buffer. In some embodiments, the wash buffer includes phosphate buffered saline. In some embodiments, the wash buffer includes saline sodium citrate.

In some embodiments, the plurality of capture probes includes one or more functional domains, a cleavage domain, a unique molecular identifier, or a combination thereof.

In some embodiments, the composition includes an organic solvent, a detergent, an enzyme, or a combination thereof. In some embodiments, the composition includes a permeabilization agent, such as, but not limited to, an endopeptidase, a protease, sodium dodecyl sulfate, polyethylene glycol tert-octylphenyl ether, polysorbate 80, and polysorbate 20, N-lauroylsarcosine sodium salt solution, saponin, TRITON-X-100™ (t-octylphenoxypolyethoxyethanol), and TWEEN-20™ (polysorbate 20). In some embodiments, the endopeptidase is pepsin. In some embodiments, the endopeptidase is proteinase K.

In some embodiments, the composition includes one or more fixatives. In some compositions, the fixative includes ethanol, methanol, acetone, formaldehyde, paraformaldehyde-Triton, glutaraldehyde, or a combination thereof. In some embodiments, the composition includes one or more stains. In some embodiments, the composition includes a hematoxylin and/or eosin stain. In some embodiments, the stain includes one or more of a detectable label selected from the group consisting of a radioisotope, a fluorophore, a chemiluminescent compound, a bioluminescent compound, or a combination thereof.

In some embodiments, the dideoxynucleotides include ddATP. In some embodiments, the dideoxynucleotides include ddTTP. In some embodiments, the dideoxynucleotides include ddGTP. In some embodiments, the dideoxynucleotides include ddCTP. In some embodiments, the dideoxynucleotides include a mixture of ddATP, ddTTP, ddCTP, and ddGTP. In some embodiments, the solution includes about 0.5 mM of the dideoxynucleotides to about 25 mM of the dideoxynucleotides. In some embodiments, the solution includes about 0.5 mM of the dideoxynucleotides to about 1.5 mM of the dideoxynucleotides. In some embodiments, the solution includes about 1 mM of the dideoxynucleotides.

In some embodiments, the solution includes $CoCl_2$. In some embodiments, the solution includes about 0.1 mM $CoCl_2$ to about 2 mM $CoCl_2$. In some embodiments, the solution includes about 0.25 mM $CoCl_2$. In some embodiments, the solution includes about 0.1 mM to about 2 mM $MgCl_2$.

In some embodiments, a capture probe of the first area is hybridized to a target nucleic acid. In some embodiments, the target nucleic acid is DNA. In some embodiments, the target nucleic acid is RNA. In some embodiments, the RNA is mRNA.

In some embodiments, a capture probe of the first area is hybridized to a ligation product (e.g., a ligation product as described herein). In some embodiments, the ligation product includes an analyte capture sequence. In some embodiments, the capture probe is hybridized to the analyte capture sequence of the ligation product.

EXAMPLES

Figure 2:
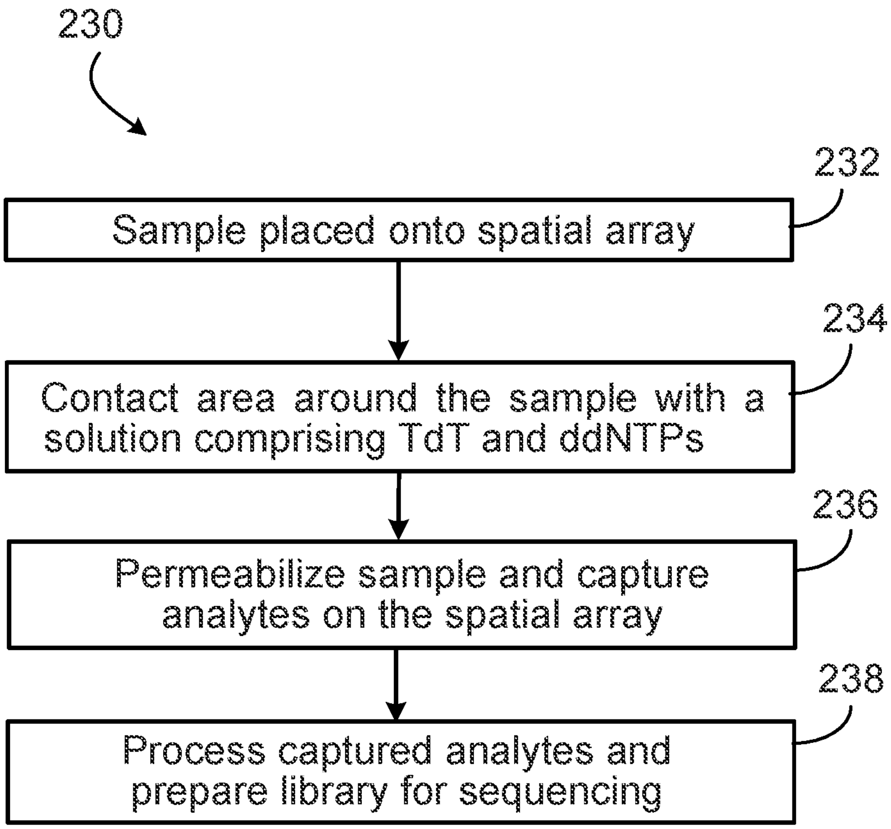
FIG. 2 shows an example workflow diagram for a method for blocking the capture probes adjacent to a biological sample on a spatial array and determining a location of a target nucleic acid in a biological sample.

Example 1: A Method for Determining a Location of a Target Nucleic Acid in a Biological Sample FIG. 2 is an exemplary workflow diagram 230 for a method of blocking the capture probes not covered by a biological sample on a spatial array and determining a location of a target nucleic acid in a biological sample. At 232 the exemplary method includes disposing a biological sample onto an array at a first area on the array, where the array includes a plurality of capture probes collectively across the first area and a second area. In the first area, a capture probe of the plurality of capture probes includes a spatial barcode and a capture domain. The second area is adjacent to the first area. For example, the second area is an area of the array not covered by the biological sample. The second area of the array also includes a capture probe of the plurality of capture probes including a spatial barcode and a capture domain, where the second area is adjacent to the biological sample disposed on the array (e.g., not covered by the biological sample).

To block capture probes in the second area of the array, a solution including terminal deoxynucleotidyl transferase and one or more dideoxynucleotides is applied to the second area of the array. At 234, the exemplary method 230 describes contacting the array (e.g., the second area of the array) with a solution including terminal deoxynucleotidyl transferase and one or more dideoxynucleotides, such that one or more dideoxynucleotides are incorporated into the capture domain of the capture probes in the second area. For example, an exemplary solution including 1.5 μl of 1 mM ddATP, 7.5 μl of $CoCl_2$ at 0.25 mM, 7.5 μl 10× terminal deoxynucleotidyl transferase reaction buffer, water, and 6 μl terminal deoxynucleotidyl transferase at 1 U/μl terminal deoxynucleotidyl transferase (NEB) is added to an array and the array is incubated at 37° C. for about 30 minutes. However, it is understood that other deoxynucleotides and divalent cationic cofactors such as $Mg^{+2}$, $Mn^{+2}$, and $Zn^{+2}$ (e.g., salts of the divalent cations) can also be utilized. After incubation, the residual solution is removed from the array. The residual solution is removed from the array by rinsing with a buffer. For example, if the biological sample is a fresh-frozen biological sample, the array is rinsed with 0.1× sodium saline citrate (SSC) buffer followed by water. If the biological sample is a fixed-formalin paraffin-embedded biological sample, the array is rinsed with 2×SSC followed by water.

Following removal of the solution, the biological sample is permeabilized. At 236, the exemplary method 230 includes permeabilizing the biological sample, such that the capture domain of the capture probe of the first area of the array hybridizes to the target nucleic acid from the biological sample.

A determination of a sequence corresponding to the spatial barcode of the capture probes in the first area is carried out. The sequence is generated with high throughput sequencing. At 238, the exemplary method 230 includes processing of the captured analyte by extending the 3' end of the capture probe using the captured analyte as a temple to generate a first strand cDNA, generating a second strand cDNA that includes a copy of the first strand cDNA, the complement of the spatial barcode of the capture probe, and other sequences as found in the capture probe, library preparation of the second strand cDNA to generate a sequencing library and determining (i) a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

The methods described in this example can also be used for the capture of proxies of analytes including, but not limited to ligation products (e.g., a ligation product as defined herein) and oligonucleotides including analyte-binding moiety barcodes and analyte capture sequences. For example, a ligation product can be a proxy for a target nucleic acid, where one or more probes hybridize to the target nucleic acid and at least one probe includes an analyte capture sequence that can hybridize to a capture domain of a capture probe. In some examples, when two probes hybridize to the target nucleic acid the two probes can be ligated to one another, thereby generating a ligation product (e.g., a proxy for the target nucleic acid). In other examples, oligonucleotides including analyte-binding moiety barcodes and analyte capture sequences can be conjugated to an analyte-binding moiety (e.g., an antibody or antigen-binding fragment thereof). The analyte capture sequence can hybridize to the capture domain of a capture probe and the analyte binding moiety barcode identifies the analyte (e.g., protein) bound by the analyte-binding moiety.

Figure 3:
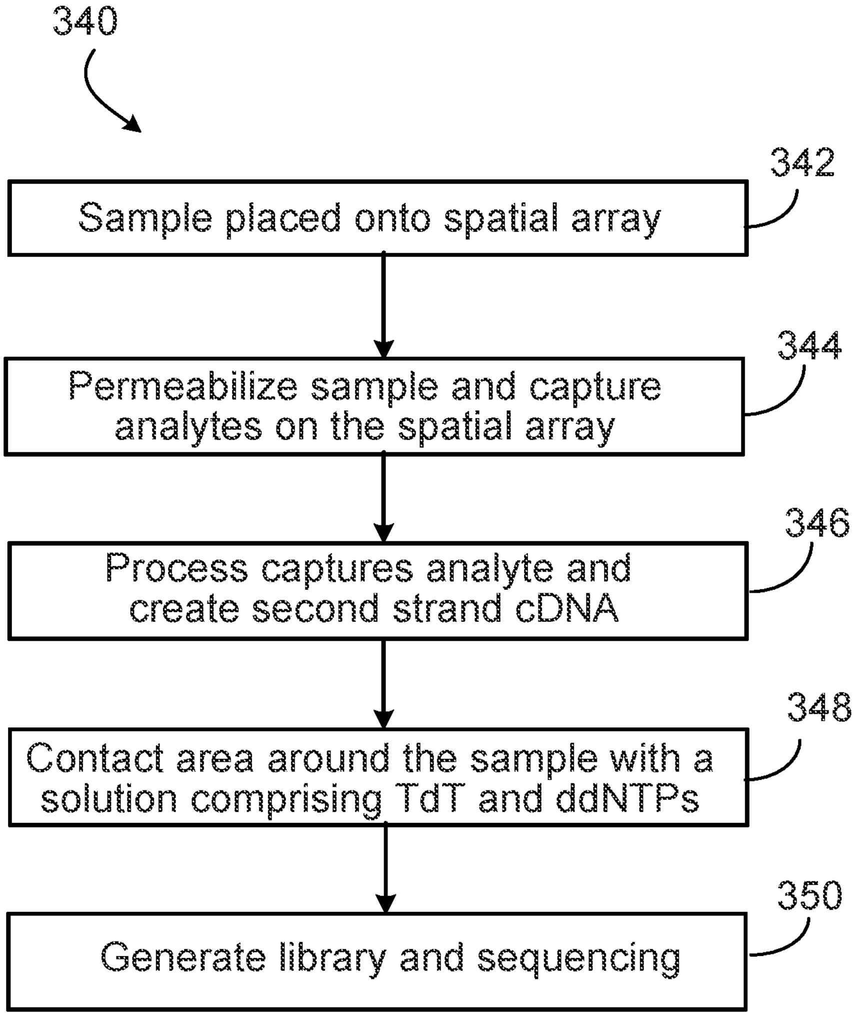
FIG. 3 shows an exemplary workflow diagram for mitigating the possibility of capture probes acting as primers and determining a location of a target nucleic acid in a biological sample.

Example 2: A Method for Determining a Location of a Target Nucleic Acid in a Biological Sample FIG. 3 is an exemplary workflow diagram 340 for a method of mitigating the possibility of capture probes acting as primers and determining a location of a target nucleic acid in a biological sample. At 342 the exemplary method includes disposing a biological sample onto an array at a first area on the array, where the array includes a plurality of capture probes collectively across the first area and a second area. In the first area, a capture probe of the plurality of capture probes includes a spatial barcode and a capture domain. The second area is adjacent to the first area. For example, the second area is an area of the array that is not covered by the biological sample. The second area of the array includes a capture probe of the plurality of capture probes including a spatial barcode and a capture domain, where the second area is not covered by the biological sample disposed on the array.

The biological sample is permeabilized 344 to allow the capture probe to hybridize to a target nucleic acid. At 344, the exemplary method 340 describes permeabilization of the biological sample and hybridization of the target nucleic acid, or proxy thereof, to the 3' end of the capture probe (e.g., the capture domain) of the first area of the array. Incubation with extension reagents can produce spatially-barcoded DNA from the captured analytes.

At 346, the capture probes are extended on the array. Extension reagents (e.g., DNA polymerase and buffer) are added to the biological sample on the array to generate a cDNA (e.g., a second strand cDNA) containing a spatial barcode complementary to the capture probe of the array.

To prevent barcode exchange that results from capture probes acting as extension templates, a solution including terminal deoxynucleotidyl transferase can be added to the array (e.g., after first-strand probe extension e.g., reverse transcription). At 348, the exemplary method 340 includes contacting the second area of the array with a solution including terminal deoxynucleotidyl transferase and one or more dideoxynucleotides, such that one or more dideoxynucleotides are incorporated to the capture domain of the capture probes in the second area. An exemplary solution includes 1.5 μl of 100 mM ddATP, 7.5 μl of $CoCl_2$ at 0.25 mM, 7.5 μl 10× terminal deoxynucleotidyl transferase reaction buffer, water, and 6 μl terminal deoxynucleotidyl transferase at 1 U/μl terminal deoxynucleotidyl transferase (NEB). It is understood that other deoxynucleotides and divalent cationic cofactors such as $Mg^{+2}$, $Mn^{+2}$, and $Zn^{+2}$ (e.g., salts of the divalent cations) can also be utilized. The solution is incubated on the array at 37° C. for 10 minutes. After incubation, the residual solution is removed from the array. The array is rinsed with 2× sodium saline citrate buffer.

A determination of a sequence corresponding to the spatial barcode, or a complement thereof, of the capture probes in the first area is determined. The sequence is generated with high throughput sequencing. At 350, the exemplary method 340 includes generating sequencing libraries from DNA probes and determining (i) a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

The methods described in this example can also be used for the capture of a ligation product (e.g., a ligation product as defined herein). For example, a ligation product can be a proxy for a target nucleic acid, where one or more probes hybridize to the target nucleic acid, are ligated to one another, and at least one probe includes an analyte capture sequence that can hybridize to a capture domain of a capture probe.

Embodiments

Embodiment 1 is a method for determining a location of a target nucleic acid in a biological sample, the method comprising: (a) disposing a non-permeabilized biological sample onto an array at a first area, wherein the first area on the array comprises a plurality of capture probes, wherein: a capture probe of the plurality of capture probes comprises a spatial barcode and a capture domain; and a second area of the array comprising a capture probe of the plurality of capture probes comprises a spatial barcode and a capture domain, wherein the second area is adjacent to the biological sample disposed on the array; (b) contacting the second area of the array with a solution comprising terminal deoxynucleotidyl transferase and one or more dideoxynucleotides, such that one or more dideoxynucleotides are added to the capture domain of the capture probes; (c) removing the residual solution from the array; (d) permeabilizing the biological sample, such that the capture domain of the capture probe of the first area of the array binds to the target nucleic acid from the biological sample; and (e) determining (i) a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

Embodiment 2 is the method of embodiment 1, wherein the removing step comprises the use of a wash buffer comprising one or more of: a solvent, an acid, a base, and a buffer.

Embodiment 3 is the method of embodiment 2, wherein the wash buffer comprises phosphate buffered saline or saline sodium citrate.

Embodiment 4 is the method of any one of embodiments 1-3, wherein the determining in step (d) comprises extending a 3' end of the capture probe of the first area of the array using the target nucleic acid as a template.

Embodiment 5 is the method of any one of embodiments 1-4, wherein the determining in step (d) comprises sequencing (i) the spatial barcode of the capture probe of the first area of the array, or a complement thereof, and (ii) all or a portion of the target nucleic acid, or a complement thereof.

Embodiment 6 is the method of embodiment 5, wherein the sequencing is high throughput sequencing.

Embodiment 7 is the method of any one of embodiments 1-6, wherein the permeabilization agent is selected from an organic solvent, a detergent, and an enzyme, or a combination thereof.

Embodiment 8 is the method of embodiment 7, wherein the permeabilization agent is selected from the group consisting of an endopeptidase, a protease sodium dodecyl sulfate, polyethylene glycol tert-octylphenyl ether, polysorbate 80, and polysorbate 20, N-lauroylsarcosine sodium salt solution, saponin, TRITON-X-100™ (t-octylphenoxypolyethoxyethanol), and TWEEN-20™ (polysorbate 20).

Embodiment 9 is the method of embodiment 8, wherein the endopeptidase is pepsin or proteinase K.

Embodiment 10 is a method of blocking capture probes adjacent to a biological sample, the method comprising: (a) disposing a non-permeabilized biological sample onto an array at a first area, wherein the first area on the array comprises a plurality of capture probes, wherein: a capture probe of the plurality of capture probes comprises a spatial barcode and a capture domain; and a second area of the array comprising a capture probe of the plurality of capture probes comprises a spatial barcode and a capture domain, wherein the second area is adjacent to the biological sample disposed on the array; and (b) contacting the second area of the array with a solution comprising terminal deoxynucleotidyl transferase and one or more dideoxynucleotides, such that one or more dideoxynucleotides are added to the capture domain of the capture probes.

Embodiment 11 is the method of embodiment 10, wherein the method further comprises permeabilizing the biological sample, such that the capture domain of the capture probe of the first area of the array binds to the target nucleic acid from the biological sample.

Embodiment 12 is the method of embodiment 11, wherein step (c) comprises contacting the non-permeabilized biological sample with a permeabilization agent, wherein the permeabilization agent is selected from an organic solvent, a detergent, and an enzyme, or a combination thereof.

Embodiment 13 is the method of embodiment 12, wherein the permeabilization agent is selected from the group consisting of: an endopeptidase, a protease sodium dodecyl sulfate, polyethylene glycol tert-octylphenyl ether, polysorbate 80, and polysorbate 20, N-lauroylsarcosine sodium salt solution, saponin, TRITON-X-100™ (t-octylphenoxypolyethoxyethanol), and TWEEN-20™ (polysorbate 20).

Embodiment 14 is the method of embodiment 13, wherein the endopeptidase is pepsin or proteinase K.

Embodiment 15 is the method of any one of embodiments 10-15, wherein the method further comprises removing the residual solution from the array prior to permeabilization.

Embodiment 16 is the method of embodiment 15, wherein the removing step comprises the use of a wash buffer comprising one or more of: a solvent, an acid, a base, and a buffer.

Embodiment 17 is the method of embodiment 16, wherein the wash buffer comprises phosphate buffered saline or saline sodium citrate.

Embodiment 18 is the method of any one of embodiments 1-17, wherein the non-permeabilized biological sample is fixed and/or stained prior to step (a).

Embodiment 19 is the method of any one of embodiments 1-18, wherein the method further comprises, between steps (a) and (b), fixing and/or staining the non-permeabilized biological sample.

Embodiment 20 is the method of embodiment 18 or embodiment 19, wherein the step of fixing the non-permeabilized biological sample comprises the use of a fixative selected from the group consisting of ethanol, methanol, acetone, formaldehyde, paraformaldehyde-Triton, glutaraldehyde, and combinations thereof.

Embodiment 21 is the method of embodiment 18 or embodiment 19, wherein the step of staining the non-permeabilized biological sample comprises the use of eosin and hematoxylin.

Embodiment 22 is the method of any one of embodiments 18-21, wherein the step of staining the non-permeabilized biological sample comprises the use of a detectable label selected from the group consisting of a radioisotope, a fluorophore, a chemiluminescent compound, a bioluminescent compound, or a combination thereof.

Embodiment 23 is a method for determining a location of a target nucleic acid in a biological sample, the method comprising: (a) disposing a biological sample onto an array at a first area on the array, wherein the first area on the array comprises a plurality of capture probes, wherein: a capture probe of the plurality of capture probes comprising a spatial barcode and a capture domain; and a second area of the array comprising a capture probe of the plurality of capture probes comprising a spatial barcode and a capture domain, wherein the second area is adjacent to the biological sample disposed on the array, wherein the capture domain of the capture probe of the first area of the array binds to the target nucleic acid; (b) extending a ligation product into the 5' end of the capture probe of the first area of the array using the capture probe as a template; (c) contacting the second area of the array with a solution comprising terminal deoxynucleotidyl transferase and one or more dideoxynucleotides, such that one or more dideoxynucleotides are added to the capture domain of the capture probes; (d) removing the residual solution from the array; and (e) determining (i) a sequence corresponding to the spatial barcode of the capture probe of the first area of the array, or a complement thereof, and (ii) all or a portion of a sequence corresponding to the target nucleic acid, or a complement thereof, and using the sequences of (i) and (ii) to determine the location of the target nucleic acid in the biological sample.

Embodiment 24 is the method of embodiment 23, wherein the removing step comprises the use of a wash buffer comprising one or more of: a solvent, an acid, a base, and a buffer.

Embodiment 25 is the method of embodiment 24, wherein the wash buffer comprises phosphate buffered saline sodium citrate.

Embodiment 26 is the method of any one of embodiments 23-25, wherein the determining in step comprises extending a 3' end of the capture probe of the first area of the array using the target nucleic acid as a template.

Embodiment 27 is the method of any one of embodiments 23-26, wherein the determining in step comprises sequencing (i) the spatial barcode of the capture probe of the first area of the array, or a complement thereof, and (ii) all or a portion of the target nucleic acid, or a complement thereof.

Embodiment 28 is the method of embodiment 27, wherein the sequencing is high throughput sequencing.

Embodiment 29 is a method of blocking capture probes to decrease barcode exchange and/or blocking capture probes to decrease the use of capture probes as primers, the method comprising: (a) disposing a biological sample onto an array at a first area on the array, wherein the first area on the array comprises a plurality of capture probes, wherein: a capture probe of the plurality of capture probes comprising a spatial barcode and a capture domain; and a second area of the array comprising a capture probe of the plurality of capture probes comprising a spatial barcode and a capture domain, wherein the second area is adjacent to the biological sample disposed on the array, wherein the capture domain of the capture probe of the first area of the array binds to the target nucleic acid; (b) extending a ligation product into the 5' end of the capture probe of the first area of the array using the capture probe as a template; and (c) contacting the second area of the array with a solution comprising terminal deoxynucleotidyl transferase and one or more dideoxynucleotides, such that one or more dideoxynucleotides are added to the capture domain of the capture probes.

Embodiment 30 is the method of embodiment 29, wherein the method further comprises removing the residual solution from the array.

Embodiment 31 is the method of embodiment 30, wherein the removing step comprises the use of a wash buffer comprising one or more of: a solvent, an acid, a base, and a buffer.

Embodiment 32 is the method of embodiment 31, wherein the wash buffer comprises phosphate buffered saline or saline sodium citrate.

Embodiment 33 is the method of any one of embodiments 23-32, wherein the biological sample is fixed and/or stained prior to step (a).

Embodiment 34 is the method of any one of embodiments 23-33, wherein the method further comprises, between steps (a) and (b), fixing and/or staining the biological sample.

Embodiment 35 is the method of embodiment 33 or embodiment 34, wherein the step of fixing the biological sample comprises the use of a fixative selected from the group consisting of ethanol, methanol, acetone, formaldehyde, paraformaldehyde-Triton, glutaraldehyde, and combinations thereof.

Embodiment 36 is the method of embodiment 35, wherein the step of staining the biological sample comprises the use of eosin and hematoxylin.

Embodiment 37 is the method of any one of embodiments 33-35, wherein the step of staining the biological sample comprises the use of a detectable label selected from the group consisting of a radioisotope, a fluorophore, a chemiluminescent compound, a bioluminescent compound, or a combination thereof.

Embodiment 38 is the method of any one of embodiments 1-37, wherein the dideoxynucleotide is ddATP or ddTTP.

Embodiment 39 is the method of any one of embodiments 1-38, wherein the solution comprises about 0.5 mM to about 25 mM of the dideoxynucleotide.

Embodiment 40 is the method of embodiment 39, wherein the solution comprises about 0.5 mM to about 1.5 mM of the dideoxynucleotide.

Embodiment 41 is the method of embodiment 40, wherein the solution comprises about 1 mM of the dideoxynucleotide.

Embodiment 42 is the method of any one of embodiments 1-41, wherein the solution further comprises $CoCl_2$.

Embodiment 43 is the method of embodiment 42, wherein the solution comprises about 0.1 mM to about 2 mM $CoCl_2$.

Embodiment 44 is the method of embodiment 42 or embodiment 43, wherein the solution comprises about 0.25 mM $CoCl_2$.

Embodiment 45 is the method of any one of embodiments 1-44, wherein the solution further comprises a buffer.

Embodiment 46 is the method of any one of embodiments 1-45, wherein the contacting step is performed for about 5 minutes to about 90 minutes.

Embodiment 47 is the method of embodiment 46, wherein the contacting step is performed for about 60 minutes.

Embodiment 48 is the method of any one of embodiments 1-47, wherein the contacting step is performed at a temperature of about 25° C. to about 45° C.

Embodiment 49 is the method of embodiment 48, wherein the contacting step is performed at a temperature of about 37° C.

Embodiment 50 is the method of any one of embodiments 1-49, wherein the removing step comprises the use of a wash buffer comprising one or more of: a solvent, an acid, a base, and a buffer.

Embodiment 51 is the method of embodiment 50, wherein the wash buffer comprises phosphate buffered saline or saline sodium citrate.

Embodiment 52 is a kit comprising: (a) a solution comprising terminal deoxynucleotidyl transferase; (b) one or more dideoxynucleotides; (c) a substrate comprising a plurality of capture probes, wherein the capture probes comprises a spatial barcode and a capture domain; and (d) instructions for performing the method of any one of embodiments 1-51.

Embodiment 53 is the kit of embodiment 52, wherein the kit further comprises a fixative selected from the group consisting of ethanol, methanol, acetone, formaldehyde, paraformaldehyde-Triton, glutaraldehyde, and combinations thereof.

Embodiment 54 is the kit of embodiment 52 or embodiment 53, wherein the dideoxynucleotide is ddATP or ddTTP.

Embodiment 55 is the kit of any one of embodiments 52-54, wherein the solution comprises about 0.5 mM to about 25 mM of the dideoxynucleotide.

Embodiment 56 is the kit of embodiment 55, wherein the solution comprises about 0.5 mM to about 1.5 mM of the dideoxynucleotide.

Embodiment 57 is the kit of embodiment 56, wherein the solution comprises about 1 mM of the dideoxynucleotide.

Embodiment 58 is the kit of any one of embodiments 52-57, wherein the solution further comprises $CoCl_2$.

Embodiment 59 is the kit of embodiment 58, wherein the solution comprises about 0.1 mM to about 2 mM $CoCl_2$.

Embodiment 60 is the kit of embodiment 58 or 59, wherein the solution comprises about 0.25 mM $CoCl_2$.

Embodiment 61 is the kit of any one of embodiments 52-60, wherein the solution further comprises a buffer.

Embodiment 62 is the kit of any one of embodiments 52-61, wherein the kit further comprises a wash buffer comprising one or more of: a solvent, an acid, a base, and a buffer.

Embodiment 63 is the kit of embodiment 62, wherein the wash buffer comprises phosphate buffered saline.

Embodiment 64 is the kit of embodiment 62, wherein the wash buffer comprises saline sodium citrate.

What is claimed is:

1. A method of blocking capture probes to decrease barcode exchange or decrease availability of capture probes as extension templates, the method comprising:

(a) disposing a biological sample onto an array at a first area, wherein the array comprises a plurality of capture probes, wherein:

a first capture probe of the plurality of capture probes comprises a spatial barcode and a capture domain, wherein the first capture probe is comprised in the first area of the array; and a second area of the array comprises a second capture probe of the plurality of capture probes comprising a second spatial barcode and a second capture domain, wherein the second area is not covered by the biological sample disposed on the array, wherein the capture domain of the first capture probe hybridizes to a ligation product; and (b) contacting the second area of the array with a solution comprising terminal deoxynucleotidyl transferase and one or more dideoxynucleotides, such that a dideoxynucleotide is incorporated into the second capture domain of the second capture probe.

2. The method of claim 1, wherein the method further comprises removing residual solution from the second area of the array.

3. The method of claim 2, wherein the removing step comprises the use of a wash buffer comprising one or more of: a solvent, an acid, a base, and a buffer.

4. The method of claim 3, wherein the wash buffer comprises phosphate buffered saline or saline sodium citrate.

5. The method of claim 1, further comprising fixing, staining, and/or imaging the biological sample.

6. The method of claim 5, wherein the biological sample is fixed with a fixative selected from the group consisting of ethanol, methanol, acetone, formaldehyde, paraformaldehyde-t-octylphenoxypolyethoxyethanol, glutaraldehyde, and combinations thereof.

7. The method of claim 5, wherein staining the biological sample comprises use of eosin and/or hematoxylin; or use of a detectable label selected from the group consisting of a radioisotope, a fluorophore, a chemiluminescent compound, a bioluminescent compound, and a combination thereof.

8. The method of claim 1, wherein the solution comprises about 0.5 mM of the one or more dideoxynucleotides to about 25 mM of the one or more dideoxynucleotides.

9. The method of claim 1, wherein the dideoxynucleotide is ddATP or ddTTP.

10. The method of claim 1, wherein the solution further comprises about 0.1 mM $CoCl_2$ to about 2 mM $CoCl_2$.

11. The method of claim 1, wherein the contacting step is performed for about 5 minutes to about 90 minutes.

12. The method of claim 1, wherein the contacting step is performed at a temperature of about 25° C. to about 45° C.

13. The method of claim 1, wherein the biological sample is a tissue section.

14. The method of claim 1, wherein the method further comprises (c) permeabilizing the biological sample, such that the capture domain of the first capture probe hybridizes to the ligation product from the biological sample.

15. The method of claim 14, wherein step (c) comprises contacting the biological sample with a permeabilization agent, wherein the permeabilization agent is selected from the group consisting of: an endopeptidase, a protease, sodium dodecyl sulfate, polyethylene glycol tert-octylphenyl ether, polysorbate 80, polysorbate 20, N-lauroylsarcosine sodium salt solution, saponin, and t-octylphenoxypolyethoxyethanol.

16. The method of claim 15, further comprising removing residual solution from the second area of the array prior to permeabilizing the biological sample.

17. A method of blocking capture probes to decrease barcode exchange or decrease availability of capture probes as extension templates, the method comprising:

(a) disposing a biological sample onto an array at a first area, wherein the array comprises a plurality of capture probes, wherein: a first capture probe of the plurality of capture probes comprises a spatial barcode and a capture domain, wherein the first capture probe is comprised in the first area of the array; and a second area of the array comprises a second capture probe of the plurality of capture probes comprising a second spatial barcode and a second capture domain, wherein the second area is not covered by the biological sample disposed on the array, wherein the capture domain of the first capture probe hybridizes to a ligation product;

(b) extending the ligation product toward the 5' end of the first capture probe using the first capture probe as a template; and (c) contacting the second area of the array with a solution comprising terminal deoxynucleotidyl transferase and one or more dideoxynucleotides, such that a dideoxynucleotide is incorporated into the second capture domain of the second capture probe.

18. The method of claim 17, wherein the ligation product is generated by hybridizing a first probe and a second probe to a target nucleic acid, wherein the first probe and the second probe are ligated to form the ligation product.

19. The method of claim 18, wherein the first probe or the second probe comprises an analyte capture sequence that hybridizes to the capture domain of the first capture probe.

20. The method of claim 17, further comprising removing residual solution from the second area of the array, wherein the removing comprises use of a wash buffer comprising one or more of: a solvent, an acid, a base, and a buffer.

* * * * *